US005955269A

United States Patent [19]
Ghai et al.

[11] Patent Number: 5,955,269
[45] Date of Patent: Sep. 21, 1999

[54] METHODS OF SCREENING FOODS FOR NUTRACEUTICALS

[75] Inventors: Geetha Ghai, Murray Hill; Charles Boyd; Katalin Csiszar, both of New Brunswick; Chi-Tang Ho, East Brunswick; Robert T. Rosen, Pottersville, all of N.J.

[73] Assignee: Rutgers, The State University of New Jersey, New Brunswick, N.J.

[21] Appl. No.: 08/670,826

[22] Filed: Jun. 20, 1996

[51] Int. Cl.[6] .............................. C12Q 1/68; C12P 19/34; A23L 1/00

[52] U.S. Cl. .................................. 435/6; 435/91.2; 435/4; 426/478

[58] Field of Search ............................... 435/91.1, 91.2, 435/91.51, 6, 7.1, 4; 426/478

[56] References Cited

U.S. PATENT DOCUMENTS

| | | | |
|---|---|---|---|
| 4,997,854 | 3/1991 | Kagan et al. | 514/660 |
| 5,252,608 | 10/1993 | Palfreyman et al. | 514/651 |
| 5,427,916 | 6/1995 | Gewirtz et al. | 435/6 |
| 5,556,754 | 9/1996 | Singer et al. | 435/6 |
| 5,620,885 | 4/1997 | Bathurst | 435/4 |
| 5,643,730 | 7/1997 | Banker | 435/6 |

OTHER PUBLICATIONS

Brostrom and Brostrom, 1993, "Calcium Homeostasis, Endoplastic Reticular Function, and the Regulation of mRNA Translation in Mammalian Cells" *Nutrition and Gene Expression* (CRC Press, Boca Raton) pp. 117–142.

Gacheru et al., 1993, "Expression and Accumulation of Lysyl Oxidase, Elastin, and Type I Procollagen in Human Menkes and Mottled Mouse Fibroblasts", Archives of Biochem. and Biophys. 301:325–329.

Glauert, 1993, "Dietary Fat, Gene Expression, and Carcinogenesis" *Nutrition and Gene Expression* (CRC Press, Boca Raton) pp. 247–268.

Hargrove and Bernadier, 1993, "Nutrient Receptors and Gene Expression" *Nutrition and Gene Expression* (CRC Press, Boca Raton) pp. 1–22.

Huang et al., 1994, "Cancer Chemoprevention by Phytochemicals in Fruits and Vegetables" *Food Phytochemicals I: Fruits and Vegetables* (American Chemical Society) pp. 2–16.

Kuivaniemi et al., 1985, "Type IX Ehlers–Danlos Syndrome and Menkes Syndrome: The Decrease in Lysyl Oxidase Activity Is Associated with a Corresponding Deficiency in the Enzyme Protein", Am. J. Hum. Genet. 37:798–808.

Augenlicht et al., 1992, "Genetic biomarkers", *Cancer Chemoprevention* (CRC Press, Inc., Boca Raton) pp. 559–569.

Bellet, 1992, "Tumor–susceptibility markers", J. Natl. Cancer Inst. Monographs 12:115–121.

Best, Jan. 1996, "Nutraceuticals suit up to play", Prepared Foods:33–35.

Betz and Fox, 1994, "High–performance liquid chromatographic determination of glucosinolates in Brassica vegetables", *Food Phytochemicals for Cancer Prevention I* (American Chemical Society, Washington DC) pp. 181–196.

(List continued on next page.)

*Primary Examiner*—Carla J. Myers
*Attorney, Agent, or Firm*—Pennie & Edmonds LLP

[57] ABSTRACT

The invention relates to an assay system for screening nutraceuticals, i.e., foods or food substances that occur naturally, or that are produced during processing which are capable of modulating in a subject the expression of one or more genes associated with a disease or undesirable physical condition. The nutraceuticals identified by the screening assays can be incorporated into compositions which may be administered to a subject to treat or prevent a disease or undesirable condition, or otherwise to improve the health of the subject. The invention further provides methods for modifying the amount of nutraceuticals in raw and processed foods or food substances.

43 Claims, 1 Drawing Sheet

OTHER PUBLICATIONS

Boyd et al., 1995, "The size heterogeneity of human lysyl oxidase mRNA is due to alternate polyadenylation site and not alternate exon usage", Mol. Biol. Reports 21:95–103.

Bronzetti, 1994, "Antimutagens in food", Trends in Food Sci. and Tech. 5:390–395.

Bulkeley, 1995, "Scientists try to make broccoli fun", The Wall Street Journal, Monday, Jul. 17.

Cooper et al., 1994, "Analysis of cucuminoids by high–performance liquid chromatography", *Food Phytochemicals for Cancer Prevention II* (American Chemical Society, Washington, DC) pp. 231–236.

Donnelly, 1995, "Genetic researchers recombine efforts with food scientists", Food & Drink Daily 5: 1–2.

Fernandes et al., 1995, "Dietary lipids and calorie restriction affect mammary tumor incidence and gene expression in mouse mammary virus/v–Ha–ras transgenic mice", Proc. Natl. Acad. Sci. USA 92:6494–6498.

Fujimura, 1994, "Diagnosis and the new genetics", Curr. Opin. in Biotech. 5:654–662.

Gerster, 1992, "Anticarcinogenic effect of common carotenoids", Internat. J. Vit. Nutr. Res. 63:93–121.

Gibson, 1995, "We are what we eat", Cereal Foods World 40:488–490.

Giovannucci et al., 1995, "Intake of carotenoids and retinol in relation to risk of prostate cancer", J. Natl. Cancer Inst. 87:1767–1776.

Gorman et al., 1982, "Recombinant genomes which express chlorophenicol acetyltransferase in mammalian cells", Mol. and Cell. Biol. 2:1044–1051.

Guardiola and Maffei, 1993, "Control of MHC class II gene expression in autoimmune, infectious, and neoplastic diseases", Critical Rev. in Immunology 13:247–268.

Ho et al., 1994, "Phytochemicals in teas and rosemary and their cancer–preventive properties", *Food Phytochemicals for Cancer Prevention II* (American Chemical Society, Washington, DC) pp. 3–19.

Holt and DuBois, 1991, "In vivo immediate early gene expression induced in intestinal and colonic mucosa by feeding", FEBS 287:102–104.

Kevin, Apr. 1995, "Phascinating Phytochemicals", Food Processing:79–81.

Kletzien and Berdanier, 1993, "Glucose–6–phosphate dehydrogenase: diet and hormonal influences on de nova enzyme synthesis", *Nutrition and Gene Expression* (CRC Press, Inc., Boca Raton) pp. 187–206.

Kikuzaki et al., 1994, "Structure of antioxidative compounds in ginger", *Food Phytochemicals for Cancer Prevention II* (American Chemical Society, Washington DC) pp. 237–243.

Kolata, 1995, "Studies suggest that genes define a person's nutrient needs", The New York Times, Thursday, Oct. 26.

Kromhout, 1993, "Contribution of epidemiology in elucidating the role of foods in cancer prevention", *Food and Cancer Prevention: Chemical and Biological Aspects* (AFRC Institute of Food Research, Norwich) pp. 24–36.

Lee et al., 1995, "Analysis of Plasma and urinary tea polyphenols in human subjects", Cancer Epidemiology, Biomarkers & Prevention 4: 393–399.

Lund, 1993, "Nutritional control of gastrointestinal hormone gene expression" *Nutrition and Gene Expression* (CRC Press, Inc., Boca Raton) pp. 91–117.

Madsen and Bertelsen, 1995, "Spices as antioxidants", Trends in Food Sci. and Tech. 6:271–277.

Magnuson and Jetton, 1993, "Tissue–specific regulation of glucokinase", *Nutrition and Gene Expression* (CRC Press, Inc., Boca Raton) pp. 143–168.

Saladin et al., 1995, "Transient increase in obese gene expression after food intake or insulin administration", Nature 377:527–529.

Sobell et al., 1992, "Delineation of genetic predisposition to multifactorial disease: a general approach on the threshold of feasibility", Genomics 12:1–6.

Velculescu et al., 1995, "Serial analysis of gene expression", Science 270:484:487.

Wattenberg, 1993, "Inhibition of carcinogenesis by nonnutrient constituents of the diet", *Food and Cancer Prevention: Chemical and Biological Aspects* (AFRC Institute of Food Research, Norwich) pp. 12–23.

Weihmuller, Mar. 1996, "Seasonings and herbs: from folklore to flavors", Prepared Foods:42–54.

Wicker–Planquart and Puigserver, 1993, "Regulation of gastrointestinal lipase gene expression by dietary lipids" in *Nutrition and Gene Expression* (CRC Press, Inc., Boca Raton) pp. 55–71.

Brand and Wang, 1988, "Gastrin Gene Expression and Regulation in Rat Islet Cell Lines", J. Biol. Chem. 263:16597–16603.

Brubaker et al., 1990, "Synthesis and Secretion of Somatostatin–28 and –14 by Fetal Rat Intestinal Cells in Culture", Am. J. Phys. 258:974–981.

Chen et al., 1989, "Molecular and Cellular Responses of Islets During Perturbations of Glucose Homeostatis Determined by In Situ Hybridization Histochemistry", Proc. Natl. Acad. Sci. USA 86:1367–1371.

Godley and Brand, 1989, "Regulation of the Gastrin Promoter by Epidermal Growth Factor and Neuropeptides", Proc. Natl. Acad. Sci. USA 86:3036–3040.

Haun and Dixon, 1990, "A Transcriptional Enhancer Essential for the Expression of the Rat Cholecystokinin Gene Contains a Sequence Identical to the –296 Element of the Human c–fos Gene", J. Biol. Chem. 265:15455–15463.

Lichtenberger et al., 1980, "Functional Responsiveness of an Isolated and Enriched Fraction of Rodent Gastrin Cells", Gastroenterology 79:447–459.

Liddle et al., 1988, "Dietary Regulation of Rat Intestinal Cholecystokinin Gene Expression", J. Clin. Invest. 81:2015–2019.

Merchant et al., 1991, "A GC–Rich Element Confers Epidermal Growth Factor Responsiveness to Transcription from the Gastrin Promoter", Mol. Cell. Biol. 11:2686–2696.

Monstein and Folkesson, 1991, "Phobol 12–Myristate–13–Acetate (PMA) Stimulates a Different Expression of Cholecystokinin (CCK) and c–fos mRNA in a Human Neuroblastoma Cell Line", FEBS 293:145–148.

Montminy et al., 1986, "Identification of a Cyclic–AMP–Responsive Element Within the Rat Somatostatin Gene", Proc. Natl. Acad. Sci. USA 83:6682–6686.

Park et al., 1989, "Somatostatin Receptors on Canine Fundic D–Cells: Evidence for Autocrine Regulation of Gastric Somatostatin", Am. J. Phys. 257:235–241.

Philippe et al., 1988, "Alpha–Cell–Specific Expresion of the Glucagon Gene Is Conferred to the Glucagon Promoter Element by the Interactions of DNA–Binding Proteins", Mol. Cell. Biol. 8:4877–4888.

Powers et al., 1989, "Somatostatin Gene Expression in Pancreatic Islet Cells Is Directed by Cell–Specific DNA Control Elements and DNA–Binding Proteins", J. Biol. Chem. 264:10048–10056.

Theill et al., 1987, "Cell–Specific Expression of the Human Gastrin Gene: Evidence for a Control Element Located Downstream of the TATA Box", Mol. Cell. Biol. 7:4329–4336.

Wang and Brand, 1990, "Islet Cell–Specific Regulatory Domain in the Gastrin Promoter Contains Adjacent Positive and Negative DNA Elements", J. Biol. Chem. 265:8908–8914.

Wu et al., 1990, "Studies of Regulation of Gastrin Synthesis and Post–Translational Processing by Molecular Biology Approaches", Ann. N.Y. Acad. Sci. 597:17–27.

Wu et al., 1991, "Regulation of Rat Antral Gastrin and Somatostatin Gene Expression During Starvation and After Refeeding", Gastroenterology 101:1552–1558.

METHODS OF SCREENING FOODS FOR NUTRACEUTICALS

FIELD OF THE INVENTION

The invention relates to a system for screening foods and food substances that occur naturally, or that are produced during processing which are capable of modulating in a subject the expression of one or more genes associated with a disease or undesirable condition, thereby preventing or treating the disease or undesirable physical condition, or otherwise improving the health of the subject.

BACKGROUND OF THE INVENTION

Disease or undesirable condition may occur in a human subject from any one or more of a long list of causes, including microbial infection, exposure to toxins, prolonged exposure to stress, and a diet that is either deficient in one or more essential substances, contains an excess of harmful substances, such as salt, fats, cholesterol, etc., or is otherwise unbalanced. Alternatively, or in addition, the onset and development of disease or undesirable condition may have a genetic component. In some cases, such as in cystic fibrosis or phenylketonuria, a genetic lesion is present at birth. In others, one or more genetic lesions, such as those resulting from exposure to various environmental toxins, may accumulate during a person's lifetime, eventually leading to diseases such as cancer.

Recent advances in molecular genetics have permitted large-scale sequencing of the human genome, and the creation of detailed genetic linkage maps. Such sequence and position information enable identification of chromosomal regions and specific gene sequences that are associated with a disease. Comparison of expression levels of these genes in normal and patient cells reveals that some of them are overexpresed, while others are underexpressed. It is apparent that development of a disease is often associated with a progressive, characteristic change in the pattern of gene expression. By studying the expression and function of these genes, molecular mechanisms that underlie the development and onset of many diseases are being elucidated. As a result, there is an accumulation of information connecting the risk or progress of a particular disease with the expression of specific gene sequences. Such information is being applied aggressively to develop new drugs, vaccines and therapeutic methods, such as gene therapy.

It is generally accepted that a diet consisting of an adequate number of calories and having sufficient levels of vitamins and minerals allows for proper function of the various systems, and is required to maintain a state of good health. In addition, it is well-established that many diseases and undesirable conditions can be prevented, slowed, or even reversed by modifying the subject's dietary intake. For example, deficiency diseases can generally be treated by supplementing the diet with the appropriate vitamin or mineral of which the subject is deficient. High blood pressure may be treated by restricting the subject's intake of sodium. Cardiovascular disease may be prevented, or its progression slowed or even reversed, by reducing dietary consumption of fats and cholesterol. In addition, a diet high in fruits and vegetables may reduce the risk of various types of cancer (Huang et al., in Food Phytochemicals for Cancer Prevention, Vol. 1, American Chemical Society, Washington, D.C. 1994, Chapter 1; Ho et al., in Food Phytochemicals for Cancer Prevention, Vol. 2, Chapter 1). See, for example, Wattenberg, (1993) in: Waldron et al. (eds.), Food and Cancer Prevention: Chemical and Biological Aspects, Royal Soc. Chem. pp. 12–23, which describes the presence in foods of blocking agents, i.e., agents that can prevent "genotoxic" compounds from reaching or reacting with critical target sites; and suppressing agents, i.e., agents that prevent the evolution of the neoplastic process in cells previously exposed to carcinogenic agents that would otherwise cause cancer. A general source of information regarding the effects of nutrition on gene expression can be found in Berdanier and Hargrove (eds.) (1993), Nutrition and Gene Expression, CRC Press, Boca Raton, Chapters 3, 4, 6, 8 and 11.

The role of diet in maintaining optimal health in a subject, and even in slowing or reversing the progression of disease or undesirable condition, has been the subject of much public attention, debate and commercial enterprise. For example, relatively little is known about the biological effects of phytochemicals, but it is widely believed that this group of compounds will assume a position like the vitamins in the future. (Kevin K, "Phascinating Phytochemicals: Foods of Tomorrow", Food Processing 1995, pages 79–81; Best, D. "Nutraceuticals Suit up to Play", Prepared Foods, January 1996, Pages 33–35; Weihmuller F., "Seasonings & Herbs: From Folklore to Flavors", Prepared Foods, March 1996, pages 42–54.) As for the consumers, supermarkets and health food stores provide many types of "organically grown" foods, as well as an ever-widening selection of vitamins, minerals, organic extracts and other supplements, many of which are touted as cures or preventatives for a wide range of ailments. However, for many of these foods or food supplements, there is little scientific basis underlying the claim that they are beneficial to health. Where data is available, it is usually derived from long-term epidemiological studies of humans, or studies in animals with defined diets.

Although the healthful effects of certain foods are known, the mechanism of their beneficial actions in disease prevention or treatment, especially at the gene level, is still poorly understood. No method is presently available to facilitate the systematic identification of foods or food substances capable of modulating expression of specific genes. Thus, in view of the numerous advances in the understanding of disease mechanisms and genomics, there is an increasing need for innovative methods that can rapidly and directly identify foods or food substances that have genuine healthful benefits. Having ascertained the effect certain foods or food substances have on gene expression, novel foods that can prevent or treat specific diseases can then be developed.

SUMMARY OF THE INVENTION

The present invention provides compositions comprising and methods for identifying foods and food substances that occur naturally or that are produced during processing which are capable of modulating in a subject the expression of one or more genes associated with a disease or undesirable condition, thereby preventing or treating the disease or undesirable condition, ameliorating the symptoms thereof, or otherwise improving the health of the subject.

In one embodiment, the present invention provides a method of screening for the presence of nutraceuticals in foods by testing for their ability to modulate the expression of one or more genes associated with a disease or undesirable condition. One method of screening comprises testing the ability of a food or food substance to modulate expression of a disease-associated gene in vitro by exposing cells in culture to the food or food substance and detecting a change in expression of the particular gene in the cells.

Another method of screening comprises testing the ability of a food or food substance to modulate expression of a disease-associated gene of a particular subject in vitro by exposing a culture of cells obtained from the subject to the food or food substance and detecting a change in expression of the particular gene. The invention further provides methods of isolation of compounds present in foods or food substances that are capable of modulating disease-related gene expression.

Another method of screening comprises testing the ability of the food or food substance to modulate expression of a disease-related gene in an animal model. Any animal model of a disease may be used, including those that are created by breeding and transgenic techniques.

In a further embodiment, the present invention provides compositions comprising one or more nutraceuticals identified according to the method of the present invention, which can be administered to a subject in need thereof in an amount sufficient to modulate expression of a disease-associated gene. Such compositions can be administered either as isolated supplements or incorporated into one or more foods.

In yet another embodiment, the present invention provides a method of increasing the healthful benefit of a food such as, for example, a plant, by identifying the presence of a nutraceutical naturally produced in the plant using the screening procedure of the present invention, and altering the amount, or otherwise modifying the characteristics, of the nutraceutical either by classical breeding methods or by genetic transformation of the plant.

DETAILED DESCRIPTION OF THE INVENTION

Figure 1:
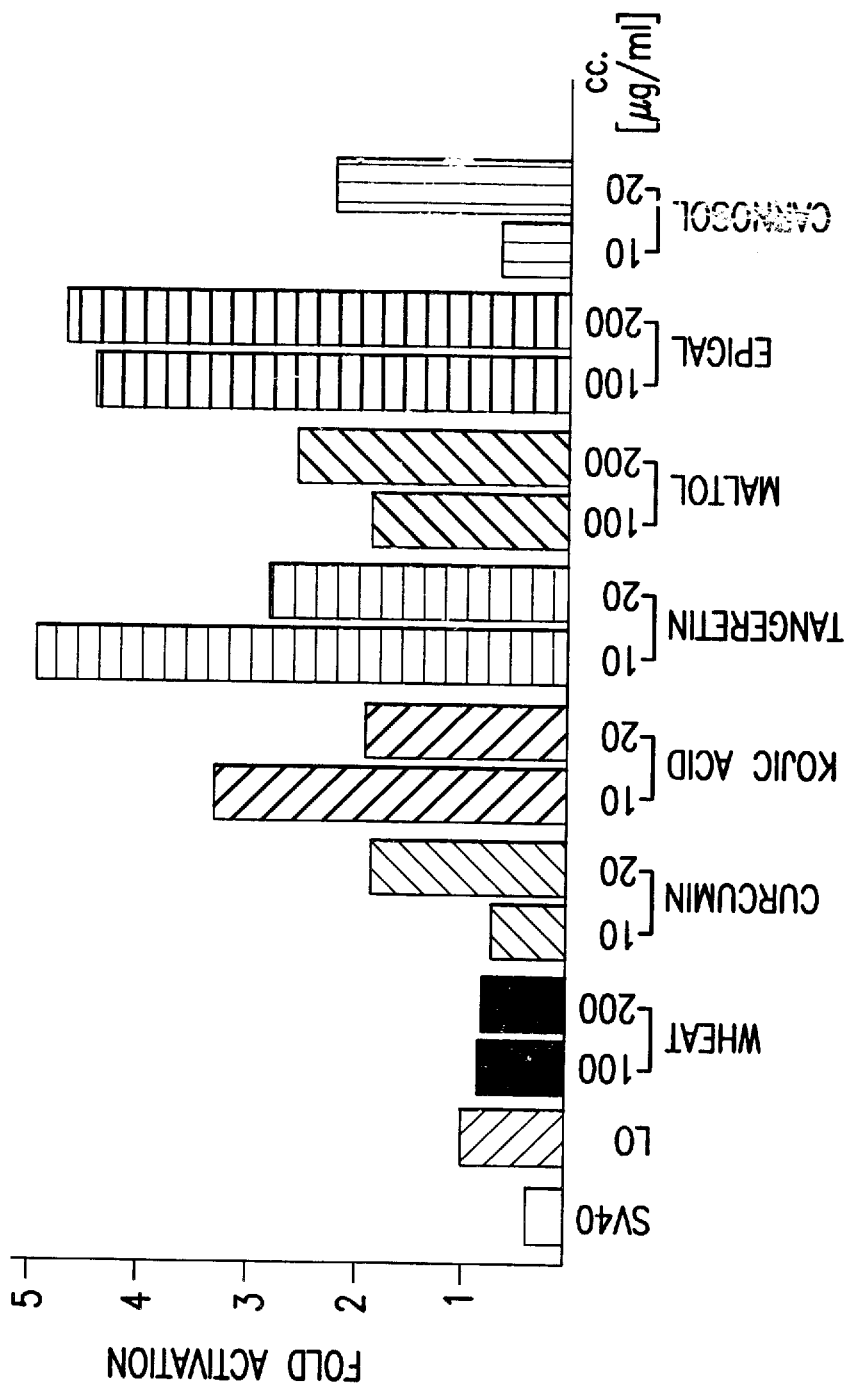
FIG. 1. Lysyl oxidase promoter activity measured as CAT activity in the presence of wheat extract (wheat), curcumin, kojic acid, tangeretin, maltol, epigallocatechin gallate (epigal.) and carnosol at the stated concentrations.

The present invention provides a system for identifying or screening foods and food substances which are capable of modulating the expression of one or more genes that are related to or associated with a disease or undesirable condition. Foods or food substances of plant or animal origin which occur naturally or which are produced during processing, and are capable of modulating the expression of one or more genes associated with a disease or undesirable condition, are designated herein as "nutraceuticals." The methods of the invention offer direct, rapid, and systematic analyses of the effect of food or food substances on the expression of specific genes.

The methods of the invention provide for the identification of foods and food substances that are capable of either: (1) down-regulating the expression of one or more genes in a subject that contribute to the onset or progression of a disease or undesirable condition or the symptoms thereof; and/or (2) up-regulating the expression of one or more genes that contribute to maintaining or improving the health of a subject, such as by preventing disease or an undesirable condition, or by ameliorating the symptoms thereof. The term "modulating" as used herein encompasses upregulating and/or downregulating of gene expression. The subject can be human, or any wild or domesticated animal.

According to the present invention, cell-based assays can be used to identify nutraceuticals. Cultured test cells containing a disease-related gene or portion thereof are contacted with a particular food or food substance, at a sufficient concentration and for a sufficient time interval for the test cells to respond to the food or food substance. After the exposure, the test cells are assayed to measure the expression of the disease-related gene. The results obtained are compared to those of control cells containing the disease-related gene or a portion thereof, which were not contacted with the food or food substance. An increase or decrease in expression of the disease-related gene in the test cell indicates that the food or food substance modulates expression of the disease-related gene. The duration of exposure depends on the nature of the food or food substance, the type of test cell, and the disease-related gene. Since a subject may be subjected to the constant and long term exposure to a particular food or food substance, in certain embodiments, long periods of incubation of test cells with a food or food substance may be carried out before the test cells are assayed for changes in the level of gene expression.

Expression of the disease-related gene may be achieved by assaying, in a cell lysate, the level of messenger RNA of the disease-related gene (e.g., by Northern blot analysis), or the level or functional activity of the disease-related gene product (e.g., by Western blot analysis). If the disease-related gene product is secreted, the culture media can be assayed for the level or functional activity of the disease-related gene product. Where a reporter gene is used, the level of messenger RNA of the reporter gene, the level of the reporter gene product, the functional activity of the reporter molecule, or the signal generated by the reporter molecule, can be used to determine the functional activity of a disease-related regulatory region.

Moreover, the cells can be examined to determine whether one or more phenotypes has been altered to resemble a normal or wild type phenotype, or a phenotype more likely to produce a lower incidence or severity of symptoms. Still further, the level and/or activity of a metabolite that is dependent on the functional activity of a disease-related gene can be used for the assay. For example, components of the signal transduction pathway of which the disease-related gene product is a part can be assayed. The activity of the disease-related signal transduction pathway itself can also be assayed.

Once a change in cellular expression of the disease-related gene as a result of exposure to a food has been detected, the assay can be used in combination with standard fractionation, analytical and purification techniques, such as those described in Section 5.4, to isolate and purify the active compound(s) in the food. Fractions of the food or food substances can be used in the screening assay to allow further purification and isolation of the active compound(s). When more than one type of nutraceutical has been identified, the different types of nutraceuticals may be added to the same cells in the assay, simultaneously or sequentially, to detect additive or synergistic effects on expression of the disease-related gene.

In another embodiment, the methods of the invention can be used to test the effect of a particular food or food substance on a variety of diseases or undesirable conditions. In this instance, a panel of disease-related genes contained in one or more test cell lines are used to analyze whether expression of the genes is modulated by the food or food substance in question.

In yet another embodiment, the methods can be applied to determine the effect of nutraceuticals on the expression of as yet unknown or uncharacterized disease-related genes. For some of the diseases or undesirable conditions, many genes or proteins are differentially expressed in abnormal cells. Many of the genes or proteins are not known or characterized. By comparing the overall pattern of expression of normal and abnormal cells, characteristic and reproducible changes in expression of certain genes and protein can be recognized. The levels of these differentially expressed genes or proteins can often be used effectively as markers of a disease phenotype. The screening assays of the invention can be used in conjunction with techniques that permit side-by-side analysis of mRNAs and proteins prepared from normal and abnormal cells. The methods of the invention allow the screening of food or food substances that affect expression of these uncharacterized genes in test cells, such that the pathological pattern of gene expression is at least partially reversed. For instance, the assays can be used to identify and isolate nutraceuticals that downregulate expression of those gene sequences or proteins that are overexpressed in abnormal cells; and likewise, the assays can be used to identify and isolate nutraceuticals capable of upregulating those gene sequences that are underexpressed in cells in a disease state.

According to an alternate embodiment of the present invention, classical or transgenic animal models can be used to identify nutraceuticals. The expression of a disease-related gene can be assayed in the cell types which are known or suspected to express the disease-related gene. Use of an animal model allows analyzing in vivo the physiological effect of nutraceuticals on disease-related gene expression systemically or at the organ level. The animal model can be used to demonstrate the overall beneficial effect of one or more nutraceuticals given alone or in combination.

The present invention also provides kits for carrying out the methods of the invention. Such kits comprise, in one or more containers, an appropriate amount of the test cells. The kits optionally further comprise in one or more containers, components of the assay regimen, such as antibodies and/or nucleic acid probes, to aid detection and/or measurement of signal generated by reporter molecules in the test cells. The kits of the invention may further comprise food substances for use as positive and negative controls. Instructions are optionally included for performance of the screening methods.

The screening assays of the invention are useful to identify foods or food substances that up-regulate the expression of one or more genes that contribute to the maintenance of, or improvement in, the health status of a subject. The increased expression of such genes may be associated with the absence, delay or reduced severity of a disease or undesirable condition. Having identified such "up-regulating nutraceuticals", the subject may then increase the intake of the particular food or food substance comprising the nutraceutical as part of an overall strategy directed to treatment or prevention of a particular disease or undesirable condition, or maintaining or improving the optimal health status of the subject.

Alternatively, the screening assays of the invention are useful to identify foods or food substances that down-regulate the expression of one or more genes that contribute to the development, onset or progression of a disease or undesirable condition in a subject. Having identified such "down-regulating nutraceuticals", the subject may increase the intake of the particular food or food substance comprising the nutraceutical(s) as part of a strategy directed to treatment or prevention of the particular disease or undesirable condition, or maintaining or improving the optimal health status of the subject.

In certain embodiments of the invention, the screening assays can be used to target a subset of the population with respect to their response to certain nutraceuticals. Different population groups may respond differently, either quantitatively or qualitatively, to the same foods or food substances. Thus, a particular food substance that acts as a powerful up-modulating nutraceutical in a group of subjects, may have less or no effect in a different group of subject. For example, a particular ethnic population may be more susceptible to allergic reaction to certain kinds of food.

To compensate for this variability, specific embodiments of the present invention contemplate the establishment of a nutraceutical screening profile for each particular subject or target population group. The screening assays can be modified to take into account genetic differences and environmental factors that differ between subjects or subsets of the population. The assay would be carried out, for example, by the subject's own cells or cells from representative individuals in a population group. The subject first provides a sample of his or her own cells. An in vitro cell culture or cell line is then established from those cells. Finally, the cells are screened to identify those foods and food substances that are most effective as nutraceuticals, thus establishing a nutraceutical profile specific to the particular subject. Such a profile can be established for people who are suffering from a disease at a particular stage, or who are specially at risk of a specific disease. Population groups can be defined according to but not limited to genetic profile, gender, age, or lifestyle. The population may also be subdivided by aspects of the subject's lifestyle, such as but not limited by exposure to occupational hazards, smoking, stress, and eating disorders including obesity.

The present invention further contemplates that, as part of an overall strategy of optimal health maintenance, or disease treatment or prevention, a subject may seek to increase the intake of both nutraceuticals that up-regulate the expression of one or more genes that contribute to maintaining or improving health status, and nutraceuticals that down-regulate the expression of one or more genes, that contribute to the onset or progression of a disease or undesirable condition. The additive or synergistic effects of foods or food substances can be more favorable, and different from those of individual food substances.

The present invention further encompasses the preparation of compositions comprising one or more nutraceuticals, which may be administered to a subject either alone or in admixture with one or more foods or food substances. The composition may comprise additionally a filler or a pharmaceutically acceptable carrier (see Section 5.5). As described in Section 5.6, the amounts and characteristics of nutraceuticals in food can be modified at the time the food is prepared or processed. In addition, the amount and characteristics of nutraceuticals may be modified by exposing the source plants or animals to certain environmental conditions, or by applying classical breeding methods or recombinant DNA techniques to the animals or plants from which the nutraceuticals in the food is originated.

The compositions and methods of the present invention are described in more detail in the following sections.

GENES ASSOCIATED WITH DISEASES OR UNDESIRABLE CONDITIONS

Any gene or functional nucleotide sequence, including any expressed sequence tag (EST), whether characterized or uncharacterized, which is associated with or related to the development, onset, progression or other manifestation of any disease or undesirable condition in human or other animal, and which expression or function may be detected, is intended to fall within the scope of the present invention.

Aberrant expression of genes or functional nucleotide sequences contribute to the onset or development of a disease or undesirable condition, and the symptoms thereof. Individuals who are heterozygous for a particular harmful polymorphism or mutant allele in one or more disease-related gene are at heightened risk of developing the disease or undesirable condition. In some instances, the levels of expression of different alleles of a disease-related gene in vivo may be different among the alleles. Thus, each allelic or polymorphic forms of the gene can be tested individually in the assays of the invention.

A large number of inherited monogenic diseases have been shown to be associated with mutations, or changes in expression in a single gene, for example, cystic fibrosis, huntington's disease, the hemophilias (coagulation factor VIII or factor IX), and hypopituitary dwarfism. Some of these monogenetic diseases are caused by a defect in the transcription mechanism of the disease-related gene and may have an effect on the expression of other genes. See, Semenza, (1994) Human Mutation 3:180–199.

Genes implicated in diseases or undesirable conditions that arise as a result of somatic mutation, germline or somatic mosaicism, or uniparental disomy and imprinting are also encompassed by the present invention. Some of the imprinted genes, for example, N-myc, IGF2, c-abl and BCR may have a role in the development of cancer (Feinberg, 1993, Nature Genet 4:110–113).

Expression of a particular gene or functional nucleotide sequence may not, by itself, cause the disease or undesirable condition, but instead may occur as but one incremental step in a multi-step process leading to the onset of the disease or undesirable condition. The deregulation of expression of one or more of these genes may initiate a sequence of biochemical and cellular events leading toward a particular disease. These multifactorial or polygenic diseases show a strong genetic component although the pattern of inheritance appears to be non-mendelian. Large scale sequencing of cDNAs and the genomes of animals, such as humans, have produced a large collection of nucleic acid sequences, some of which are fragments of protein-coding genes (Adams et al., 1995, Nature, vol. 377, issue 6547S, Genome Directory, page 3S–174S). Genetic linkage analysis and positional cloning techniques have been used to map or identify genes, expressed sequence tags or functional nucleotide sequences that are contributory to the predisposition, development and progression of such multifactorial genetic diseases (Sobell et al., 1992, Genomics 12:1–6; Fujimura, 1994, Curr Opin Biotechnol 1994, 5:654–662).

According to the present invention, if the expression or function of a disease-related gene, expressed sequence tag, or genetic marker, including allele or polymorphic variant thereof, can be detected and measured, it can be used in the screening assays of the present invention for identifying nutraceuticals.

In specific embodiments, the methods of the invention may be used to identify nutraceuticals that would be useful in treating, controlling or preventing the following non-limiting examples of diseases: cancer, cardiovascular diseases, respiratory diseases, diseases of the kidney, liver and pancreas, gastrointestinal diseases, hematological diseases, metabolic diseases, neurological diseases, diseases of the immune system, endocrine system, and reproductive systems, and infectious diseases. Undesirable conditions that can be treated, ameliorated or prevented by nutraceuticals may include but not limited to fatigue; obesity; infertility; physical changes associated with aging; pregnancy; menopause; allergy; transplant rejection; wounds; sleep disorders; substance dependence; and behavioral disorders. The choice of genes to be used in the screening assays of the invention can be determined by the biology of the disease, and the function of genes in the disease process. Those skilled in the art would know which gene(s) is associated with a particular disease or undesirable condition, and hence, useful in the present invention.

Moreover, the subject receiving the nutraceutical may not have the disease, but may be at risk of developing the disease. Such risk may include genetic risks, such as high incidence of the disease in the family; or being heterozygous for a particular genotype that is predisposing to the disease; or environmental risks, e.g., smoking or exposure to carcinogens.

Some of the exemplary disease-related genes that can be used in the present invention are discussed below.

Cancer is characterized primarily by an increase in the number of abnormally growing cells derived from a given normal tissue, and invasion of adjacent tissues by these abnormal cells. Clinical data and molecular biologic studies indicate that cancer is a multistep process that is associated with minor changes in gene structure and/or gene expression.

Cancers that can be treated, controlled or prevented by nutraceuticals identified by the methods of the present invention are sarcomas, carcinomas, solid tumor, nonsolid tumor, metastatic cancers, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma, oesophagal cancer, stomach cancer, colorectal cancer, pancreatic cancer, adenocarcinoma, renal cell carcinoma, hepatoma, choriocarcinoma, Wilms' tumor, small cell lung carcinoma, epithelial carcinoma, medulloblastoma, hemangioblastoma, neuroblastoma, retinoblastoma; leukemias, e.g., acute lymphocytic leukemia and acute myelocytic leukemia; chronic leukemia, lymphoma, Hodgkin's disease and non-Hodgkin's disease.

Mutations in both tumor suppressor genes and proto-oncogenes have been shown to be generally responsible for the pathogenesis of cancer. Activation or overexpression of proto-oncogenes produces a "gain of function" in the cancer cells. A large number of such proto-oncogenes encode growth factors and their receptors, and signal transducing molecules, e.g., erb, sis, fos, jun, ras. According to the present invention, nutraceuticals that are capable of down-regulating the expression of these genes are useful in the prevention and treatment of the cancer.

On the other hand, inactivation or underexpression of tumor suppressor genes produces a "loss of function" in the cancer cells. These genes include but are not limited to the BRCA1 (breast cancer gene 1, Miki et al., 1994, Science 266:66–71; BRCA2, Wooster et al., 1994, Science 265:2088–2090); retinoblastoma gene (Rb; Friend et al., 1986, Nature 323:643–646); p53 (Malkin et al., 1990, Science 250:1233–1238); NF2 (neurofibromatosis type 2; Rouleau et al., 1993 Nature, 363:515–521); MTS1 (melanoma cdc p16; Kamb et al., 1994, Science 264:436–440); DCC (Deleted in Colon Cancer); APC (Adenomatous Polyposis Coli; Groden et al., 1991, Cell 66:589–600); MCC; FHIT; PTC and lysyl oxidase (LOX; Boyd et al., 1995, Mol. Biol.

Reports 21:95–103). Some tumor suppressor genes appear to be important in cell cycle regulation, and DNA repair. According to the present invention, by up-regulating the level of expression of these tumor suppressor genes through the ingestion of a nutraceutical, cancer caused by changes in these genes may be prevented or treated.

Any of the proto-oncogenes, tumor suppressor genes and cancer-related genes, such as those involved in cell cycle control, DNA repair, signal transducing phosphorylation cascades, and transcription factors and cofactors may be used in the screening assays of the invention. An example using the human lysyl oxidase (LOX) gene in a screening assay is provided in Section 6 to illustrate the method of the present invention. LOX is an enzyme critical to the formation of elastic fibrils and collagen fibers. LOX also acts as a ras-mediated tumor suppressor. Mutation in LOX and other tumor suppressor genes such as ras, p53, DCC, APC and MCC in the colonic epithelium will lead to the development of dedifferentiated hyperplastic cells that can become metastatic rapidly. In addition, activity of the LOX gene, or a lack thereof, has been implicated in various disease states, such as Ehler-Danlos syndrome, Marfan's syndrome, and Menkes syndrome. See, for example, U.S. Pat. No. 4,997,854 and U.S. Pat. No. 5,252,608.

Mutations in transcriptional factors, or cofactors that are involved in regulation of gene expression tend to have have pleiotropic effects because each transcription factor or cofactor can be involved with regulation of multiple genes. For several transcriptional factors, germline mutations have been shown to result in malformation syndromes, whereas somatic mutations in these genes contribute to the multistep process of tumorigenesis. Genes encoding such factors, such as but not limited to Sp-1, GATA-1, Pit-1, HOX gene products (McGinnis et al., 1992, Cell 68:283–302), the zinc finger family of proteins, and the leucine zipper family of proteins (Busch et al., 1990, Trends Genet 6:36–40) may also be used in the assays of the invention.

The destruction or disruption of the body's own tissues by the immune system results from a complex interaction of genetic and environmental factors. Such damage could arise as a result of, for example, acute and chronic inflammation; ischaemia; transplantation; and autoimmune diseases, e.g., insulin-dependent diabetes, multiple sclerosis, systemic lupus erythematous and rheumatoid arthritis. Upregulation of HLA class II gene expression has been observed on target tissues of most autoimmune diseases (Guardiola et al., 1993, Critical Rev Immunol 13:247–268). The damage is often associated with and can be caused by systemic upregulation of acute phase proteins; production of autoantibodies; cytokine secretion; complement activation; induction of cell adhesion molecules; and infiltration of body tissues by blood derived cells, such as activated macrophages, plasma cells, and neutrophils. See also Elasser-Beilen et al., 1993, Tumor Biol. 14:69–94; Wordsworth et al., 1995, Br Med Bulletin 51:249–266.

Any of the genes that encode immune response effector molecules, acute phase proteins, cytokines and their receptors, cell adhesion molecules, and molecules involved in signal transduction underlying the immune response can be used in the screening assay. Since some of the gene products will have a pro-inflammatory effect, the screening assays can be designed to detect downregulation of such genes by nutraceuticals. Such pro-inflammatory genes may include IL-1, IL-6, tumor necrosis factor, the selecting, the integrin α and β chains, complement proteins, matrix metalloproteases, enzymes involved in prostaglandin metabolism, and MHC class I and II molecules. Similarly, the assays can be designed to identify nutraceuticals that upregulate genes that have an anti-inflammatory influence. Such genes may include but are not limited to complement receptor 1, IL-10, and IL-1 receptor antagonist.

The epidemiology of obesity and studies of mouse models strongly suggest that the disorder exhibits inherited characteristics (Stunkard, 1990, N. Eng. J. Med. 322:1483; Moll et al. 1991, Am. J. Hum. Gen. 49:1243). A number of genes implicated in obesity have recently been identified and can be used in the present invention, for example, the leptin gene (Zhang, Y. et al., 1994, Nature 372:425–432); the receptor for leptin (Tartaglia et al., 1995, Cell 83:1263), and the carboxypeptidase E gene related to the fat mutation in mice (Naggert, J. K., et al., 1995, Nature Genetics 10:135–141). Other genes involved in carbohydrate/fat metabolism and diabetes such as insulin and its receptor; insulin like growth factors, their receptors and their binding proteins are also candidates for use in the screening assays (Ullrich et al., 1985, Nature 313:756–761; Nissley et al., 1991, Growth factors 5:29–43; Jones et al., 1995, Endocrine Rev, 16:3–34).

Hypertension is a common multifactorial vascular disorder that is in part genetically determined. At least 10 genes have been shown to alter blood pressure by changing salt and water reabsorption in the kidney (Lifton, 1996, Science 272:676–680). Such genes encoding, e.g., angiotensinogen (Caulfield et al., 1994, New England J Med 330:1629–1633), renin, angiotensin converting enzyme (Cambien et al., 1992, Nature 359:641–644), may be used in the methods of the invention to test for nutraceuticals that have an effect on blood pressure.

Atherosclerotic vascular disease is very common, and frequently leads to death from coronary artery disease or stroke. Genetic studies of rare inherited disorders of cholesterol metabolism and vascular functions have identified a number of genes that are implicated in the pathogenesis of the disease (Keatings et al., 1996, Science 272:681–688; Gibbons et al., 1996, Science 272:689–693). Such genes may encode lipoproteins, enzymes involved in lipid metabolism, cell adhesion molecules, coagulation and fibrinolytic factors, cytokines, structural proteins of the endothelium and extracellular matrix. Non-limiting examples of such genes include LDL receptor, apolipoprotein B, apolipoprotein E, thrombin, cystathionine synthase, vascular-endothelial growth factor, elastin, VCAM-1, nitric oxide synthase, IL-1, gpIIb/IIIa and platelet activating factor. Any such genes can be used in the screening assays of the present invention.

A number of undesirable deterioration of physiological functions associated with aging have been shown to be associated with changes in expression of certain genes (Thakur et al., 1993, Mech Ageing Dev, 66:283–298). Any such gene or nucleotide sequence that are directly or indirectly involved in the process of senescence may be used in the assays of the present invention. For example, a large proportion of senile dementia in individuals are associated with the specific pathologic characteristics of Alzheimer's disease. The genes that have been implicated as causes of familial Alzheimer's disease, such as but are not limited to the βAPP gene, S182 gene (Sherrington et al., 1995 Nature 375:754–760); STM2 gene (Levy-Lehad et al., 1995, Science 269:973–977); and apolipoprotein E gene, can be used in assays to screen for nutraceuticals.

In genetic studies of substance dependence, one form of the D2 dopamine receptor gene (A1) shows a high prevalence in alcoholics, and possibly in individuals with cocaine dependence. Individuals with this A1 allele appear to have fewer receptors (Noble, 1993, Behavior Genetics, 23:119–129). Thus, genes encoding neurotransmitter receptors, such as but not limited to the D2 dopamine receptor (DRD2) can be used in the methods of the present invention. Other genes that has been shown to have an effect on behavior in rodent models may also be used, e.g., neuronal nitric oxide synthase and monoamine oxidase A have an effect on aggressiveness (Nelson et al., 1995, Nature, 378:383–386; Cases et al., 1995, Science 268:1763–1766).

A disease-related gene or portion thereof, and the regulatory sequences can be obtained from private or public deposits, or by conventional cloning or synthetic methods. Alternatively, such DNA sequences can be generated by the polymerase chain reaction (PCR), and cloned by routine molecular cloning techniques.

Briefly, genomic DNA or cDNA containing the disease related gene sequences can be purified from human cells or cells of the test organism using standard DNA purification methods. Primers for amplification can be synthesized corresponding to the known 5' and 3' boundaries of the promoter regions with additional sequences of restriction sites to facilitate subcloning. The amplification reactions are carried out in a thermal cycler under conditions determined to be acceptable for the selected template and primers. The reaction products are separated by agarose gel electrophoresis, and subcloned in a cloning vector. Where only the regulatory regions of a disease-related gene is amplified, the amplified regulatory sequences can then be recloned into an expression vector in a position relevant to the expression of the reporter gene (which is usually the 5' end of the reporter gene). As described in detail in the next section, the resulting expression construct or reporter construct containing the disease-related gene or a portion thereof, can be introduced into a batch of test cells by conventional methods, such as transformation, transfection or electroporation. Once clones of test cells containing a reporter construct have been identified, the clones can be used to create permanent test cell lines. Such cell lines can be propagated to supply test cells for large-scale screening, and for the test kits of the invention.

TEST CELLS AND GENE EXPRESSION SYSTEMS

According to the present invention, nutraceuticals can be identified by detecting a change in expression of a disease-related gene in a test cell which change results from exposure to a nutraceutical.

The term "disease-related gene or portions thereof" as used herein refers to (1) a nucleic acid molecule having a nucleotide sequence that encodes a disease-related protein or portions thereof, and/or (2) a nucleic acid regulatory region, such as a promoter, terminator or enhancer, which functionally controls expression of the nucleotide sequence that encodes a disease-related protein. The gene or functional nucleotide sequences can be derived from the nucleus as well as other organelles, such as the mitochondria. Human disease-related genes are preferred.

Any type of cell can be used in the screening assays of the invention, including cells directly obtained from a subject, and cells that have been cultured in vitro and/or genetically engineered. The term "test cell" as used herein broadly encompasses cells of prokaryotic and eukaryotic organisms, such as bacteria, yeasts, animals, and humans, that contain a disease-related gene of interest.

In one embodiment, a non-recombinant cell containing a naturally occurring disease-related gene, the expression of which can be modulated by a nutraceutical, can be used in the screening assays. Preferably, these cells are derived from the tissue or organ in which pathologic changes associated with the disease of interest are known to occur. The test cells can be primary culture cells, cells derived from tissue explants, or cells from established cell lines.

In another embodiment, the test cell can be a genetically engineered cell that contains a disease-related gene of interest or portions thereof, the expression of which can be modulated by a nutraceutical. The genetically engineered cells can be transiently transfected or permanently transformed with a recombinant expression construct containing the disease-related gene or portions thereof.

In yet another embodiment, the test cells can be genetically engineered cells that contain a reporter gene operably associated with the regulatory region of a disease-related gene, in which the expression of the reporter gene can be modulated by a nutraceutical. A reporter gene encodes a reporter molecule which is capable of directly or indirectly generating a detectable signal. The effect of a nutraceutical on the transcriptional and/or translational activity of the regulatory region of a disease-related gene can be determined by monitoring the signal generated by the expressed reporter molecule.

Furthermore, the test cells can be genetically engineered cells that express a fusion protein comprising a disease-related gene product, or a portion thereof, and a reporter moiety that renders the expression of the fusion protein in the test cells detectable. In these test cells, the coding regions of the disease-related gene and the reporter gene are joined such that the translation frame is maintained, and that expression of the fusion protein in the test cells can be modulated by a nutraceutical.

In a test cell, a disease-related gene can consist of the entire transcriptional unit including 5' untranslated regions, coding regions, introns, and 3' untranslated regions, or only portions thereof. The disease-related gene can also be complementary DNA (cDNA) or portions thereof. Any allelic, variant, polymorphic or mutant form of a disease-related gene can be used in the screening assay. A homologue of a human disease-related gene can be used if the homologous gene is regulated, and functions similarly in the organism from which the homologous gene is derived. A human disease-related gene can be introduced into a non-human host cell to generate test cell for use in the screening assay of the invention.

The regulatory regions of a disease-related gene may include those 5' non-coding sequences involved with initiation of transcription and translation, such as the TATA box, capping sequence, GC-rich sequences, other cis-acting sequences and the like (Breathnach et al., 1981, Ann Rev Biochem 50:349–383; Briggs et al., 1986, Science 234:47–52). These regulatory DNA sequences bind transcriptional factors, such as but not limited to proteins containing the helixloop-helix motif, HOX gene products, the zinc finger family of proteins, and the leucine zipper family of proteins. The non-coding region 3' to the coding sequence may also be retained for its transcriptional termination regulatory sequences, such as terminators and polyadenylation sites. Enhancers which are position- and orientation-independent sequence elements that aid transcription are also included (Thompson et al., 1992, Trends Genet 8:232–236). Other regulatory regions that can be also used in the assays may include but are not limited to negative regulators (reviewed by Renkawitz, 1990, Trends Genet 6:197); and locus control elements, such as the chromosomal region that control expression of the β-globin gene cluster (Townes, 1990, Trends Genet 6:219–223).

Test cells or host cells can be obtained from humans or animals, commercial suppliers, private laboratory deposits, and public culture collections such as the American Type Culture Collection. Test cells can be prepared from primary culture or tissue explant derived from individuals or animals by techniques well known in the art. For example, in the fibroblasts from both Menkes syndrome patients and the tortoise-shell mouse, the murine analog of Menkes syndrome, reduced LOX enzyme levels were shown to parallel the reduced recovery of steady state levels of LOX messenger RNA (Kuivaniemi et al., 1985, Am J Hum Genet 37:798–808; Gacheru et al., 1993, Arch Biochem Biophys, 301:325–329). Other examples, may include but not limited to human umbilical vein endothelial cells and human smooth muscle cells. Such cells may be further modified by techniques known in the art for specific uses. However, a permanent test cell line is preferred for convenience of handling, and consistency in genotype and phenotype. Prokaryotic cells, which are more robust to handle, can also be used.

Where the cells are to be genetically engineered, it is preferable that the host cells have been used for expression of heterologous genes, and are reasonably well characterized biochemically, physiologically, and/or genetically. It is also preferable that the host cells are of a similar cell type to those that are involved in the onset and progression of the disease of interest, especially where the disease-related gene is expressed in a tissue-specific or developmentally-regulated manner. For example, various cell lines at different stages of malignancy (e.g. HL-60 cells) can be used as host cells to express cancer-related genes which are suspected to be overexpressed or underexpressed at the corresponding stage of malignancy.

The test cells can be cultured under standard conditions of temperature, incubation time, and media composition. However, conditions for maintenance may be different from those for performing a screening assay. Modified culture conditions and media can also be used to emulate some environmental factors. For example, chemical carcinogens can be included in the culture media prior to performing an assay, or during an assay. The appropriate culture condition for a particular test cell can be determined by routine techniques well known in the art.

A host cell can be chosen which modifies and processes the expressed disease-related gene product in a specific fashion similar to that which occurs in vivo. Such modifications (e.g., glycosylation, prenylation) and processing (e.g., cleavage) of protein products can be important in the development and progression of the disease of interest. Different host cells have characteristic and specific mechanisms for the post-translational processing and modification of proteins. Appropriate cell lines can be chosen to match the cells in vivo in which pathologic changes occur in the course of the disease. Preferred mammalian host cells include but are not limited to those derived from humans, monkeys and rodents, such as HeLa, 293, $HOS_1$ fibroblast, chinese hamster ovary (CHO) cells, NIH/3T3, COS, VERO. See Kriegler M. in "Gene Transfer and Expression: A Laboratory Manual", New York, Freeman & Co. 1990.

Any host-vector systems known in the art can be used in the present invention to introduce a disease-related gene into a host cell. A cloning vector or expression vector can be used to introduce a disease-related gene into a host cell to generate test cell for the screening assay of the invention. A reporter construct is an expression vector containing one or more reporter gene sequences operably associated with one or more disease-related regulatory regions. A variety of vectors can be used which include, but are not limited to, plasmids; cosmids; phagemids; and artificial chromosomes. Alternatively, a disease-related gene or reporter construct can be introduced into the genome of the host cell by homologous recombination.

Standard molecular biology techniques can be used to prepare expression constructs containing the transcriptional and translational control signals of the disease-related gene, disease-related gene nucleotide sequence, reporter gene sequence, or sequence encoding a fusion protein. These methods include, for example, in vitro recombinant DNA techniques, synthetic techniques, and in vivo genetic recombination. The procedures described in standard treatises, e.g., Maniatis et al. 1989, Molecular Cloning, 2nd Edition, Cold Spring Harbor Press, New York; and Ausubel et al., Current Protocols in Molecular Biology, Greene Publishing Associates and Wiley Interscience, New York, which are incorporated herein by reference in their entirety, may be followed to carry out such routine molecular biology reactions.

"Operably-associated" refers to an association in which the disease-related regulatory regions and the DNA sequence to be expressed are joined and positioned in such a way as to permit transcription. Two or more sequences, such as a promoter and any other nucleic acid sequences are operably-associated if transcription commencing in the promoter will produce an RNA transcript of the operably-associated sequences. In order to be "operably-associated" it is not necessary that two sequences be immediately adjacent to one another. Therefore, a reporter gene sequence may be added to the 3' end of a disease-related gene to facilitate detection if the disease-related regulatory regions have not yet been fully characterized.

An expression vector useful in the invention may also contain selectable or screenable marker genes for initially isolating, identifying or tracking test cells that contain foreign DNA. The expression vector may also provide unique or conveniently located restriction sites to allow severing and/or rearranging portions of the DNA inserts in an expression construct. More than one disease-related gene or reporter gene may be inserted into an expression vector such that the test cell containing the resulting expressed construct can be used for testing within a single culture the effect of nutraceuticals on multiple disease-related genes.

In mammalian host cells, a variety of mammalian expression vectors are commercially available. In addition, a number of viral-based expression systems can be utilized. In cases where an adenovirus is used as an expression vector, the donor DNA sequence can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (e.g., See Logan & Shenk, 1984, Proc. Natl. Acad. Sci. (USA) 81:3655–3659). Viral vectors based on retroviruses can also be used (Morgenstern et al. 1989, Ann Rev Neurosci, 12:47–65). Alternatively, the vaccinia 7.5K promoter can be used. (See, e.g., Mackett et al. 1982, Proc. Natl. Acad. Sci. (USA)

79:7415–7419; Mackett et al. 1984, J. Virol. 49:857–864; Panicali et al. 1982, Proc. Natl. Acad. Sci. 79:4927–4931)

A number of selection systems can be used for mammalian cells, including but not limited to the Herpes simplex virus thymidine kinase (Wigler, et al. 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al. 1980, Cell 22:817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler, et al. 1980, Natl. Acad. Sci. USA 77:3567; O'Hare, et al. 1981, Proc. Natl. Acad. Sci. USA 78:1527); gpt, which confers resistance to mycophenolic acid (Mulligan & Berg, 1981), Proc. Natl. Acad. Sci. USA 78:2072); neomycin phosphotransferase (neo), which confers resistance to the aminoglycoside G-418 (Colberre-Garapin, et al. 1981, J. Mol. Biol. 150:1); and hygromycin phosphotransferase (hyg), which confers resistance to hygromycin (Santerre, et al. 1984, Gene 30:147).

Any reporter gene system known in the art can be used in the present invention. The chloramphenicol acetyltransferase (CAT) gene (Gorman et al., 1982, Mol Cell Biol, 2:1044; Prost et al., 1986, Gene 45:107–111) is a well known reporter gene that can be used in the method of the present invention as illustrated in Example 6 provided hereinbelow. Various types of isotopic and nonisotopic CAT assays that measure the kinetics of CAT activity in crude cell extracts are well known in the art and can be used in the method of the present invention (Seed et al., 1988, Gene 67:271–277). Any enzymatic reporter molecules can be used, which include but are not limited to β-galactosidase (LacZ, Nolan et al. 1988, Proc Natl Acad Sci USA 85:2603–2607), and alkaline phosphatase (Berger et al., 1988, Gene 66:1–10; Cullen et al., 1992, Methods in Enzymol, 216:362–368), which can be used with chromogenic and fluorogenic substrates. Light-emitting reporter such as bioluminescent, chemiluminescent or fluorescent proteins can also be used, which includes but are not limited to the green fluorescent protein (GFP) of $Victoria\ aequoria$ (Chalfie et al. 1994, Science 263:802–805), a modified GFP with enhanced fluorescence (Heim et al. 1995, Nature 373:663–4), the luciferase (luxAB gene product) of $Vibrio\ harveyi$ (Karp, 1989, Biochim Biophys Acta 1007:84–90; Stewart et al. 1992, J Gen Microbiol, 138:1289–1300), and the luciferase from firefly, $Photinus\ pyralis$ (De Wet et al. 1987, Mol Cell Biol 7:725–737). Any antigenic peptide or protein that can be detected by an antibody can be used as a reporter, for example, growth hormone (Selden et al., Mol Cel Biol, 6:3173). To facilitate detection by antibody binding, antigenic reporter molecules that are secreted or attached on the test cell surface are preferred.

A fusion protein comprising a disease-related gene product or a portion thereof, and a reporter moiety can be used in the methods of the present invention. An expression construct comprising a fusion gene encoding a fusion protein can be created by ligating the coding region of the disease-related gene to that of the reporter gene while the translation frame is maintained. The disease-related gene can be joined to any sequence that encodes the reporter moiety which allows the resulting fusion protein to be detected. Such amino acid sequence can encode an enzyme, fluorescent protein, chromogenic protein, or an antigenic peptide that can be detected by an antibody. A commonly used reporter gene is the $E.\ coli$ β-glucuronidase gene (GUS; Gallagher, 1992, in "GUS protocols", Academic Press) which is used with various histochemical and fluorometric substrates, such as X-glucuronide and 4-methylumbelliferyl glucuronide.

To facilitate detection, fusion proteins that are secreted, or attached on the test cell surface, are also within the scope of the invention.

The present invention also encompasses use of any animal model of human disease for identifying and testing nutraceuticals. Initially, outbred animals, such as CF-1 mice (Charles River Laboratories) can be used to examine a broad range of foods or food substances. Inbred strains, such as BALB/c, C57BL/6 and DBA/2 mice, can be used to mimic population groups so as to test the effect of the subject's genotype on its response to a nutraceutical. For a particular disease, established animal models can be used to directly correlate the expression level of the gene, the progression of the disease state, and the effect of the nutraceutical. For example, the ICR/IIa strain of mice that are highly susceptible to spontaneous or induced colon cancer may be used (Jacoby et al., 1994, Genomics 22:381–387).

Routes of delivery will vary depend on the gene and tissue that is typically affected by the disease. The nutraceutical may be administered to the test animal by means conventional to pharmaceutical testing as described in Section 5.5. Alternatively, the effect of nutraceuticals can be tested by feeding the test animal foods or food supplements containing the nutraceutical. By taking cell samples from various tissues and organs at various time intervals after ingestion or administration of the nutraceutical, the time and location of changes in the expression of a disease-related gene can be analyzed. Essentially, one can determine when and where the expression of one or more disease-related genes are modulated as a result of nutraceutical intake. In order to detect the synergistic effects of various nutraceuticals, more than one nutraceuticals can be tested simultaneously in the animal models. The animal model can also be used for testing dietary regimens that allow timely and dosed delivery of nutraceuticals to the subject animal. Test animals can be kept to provide test cells for use in the in vitro screening assays. Test cells obtained from various tissues and organs of the test animal can be maintained in culture, and then exposed directly to foods or food substances.

Transgenic animals may also be used similarly for screening and testing nutraceuticals. Animals of any species, including, but not limited to, mice, rats, rabbits, guinea pigs, pigs, micro-pigs, goats, and non-human primates, e.g., baboons, monkeys, and chimpanzees can be used to generate transgenic animals which express the disease-related gene transcript, gene product, reporter molecule, or fusion protein.

Any technique known in the art can be used to introduce a transgene comprising one or more disease-related genes or portions thereof, including reporter constructs, into animals produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety. When more than one disease-related gene is intended to be assayed, a single transgenic construct comprising multiple transgene transcriptional units can be used.

The present invention provides for transgenic animals that carry the disease-related transgene in all their cells, as well as animals which carry the transgene in some, but not all their cells, i.e., mosaic animals. The transgene can be integrated as a single transgene or in concatamers, e.q., head-to-head tandems or head-to-tail tandems. When it is desired that the disease-related transgene be integrated into a chromosomal site, gene targeting is preferred. Briefly, when such a technique is to be utilized, vectors containing some nucleotide sequences homologous to an endogenous gene or chromosomal region are designed for the purpose of integrating, via homologous recombination, into the endogenous gene or chromosomal region. The endogenous gene can be a gene homologous to the disease-related gene or any other genes.

Test cells of the invention are maintained and handled by standard cell culture procedures. To facilitate high throughput screening, the test cells can be cultured and assayed in multi-well plates in an ordered array. Typically, the individual cultures are inoculated and allowed to grow in the wells under the appropriate conditions. A coded master plates can be made and used as an archival source to replicate each culture separately into one or more working plates. The coded archival plates can be sealed and stored for future use. Manipulations of the cultures and fluid handling can be done with a multi-channel devices. Most of the transfers and manipulations can be automated, and performed by laboratory robots.

Test cell lines generated by the above-described methods for the screening assays may be expanded, stored and retrieved by any techniques known in the art that is appropriate to the test cell. For example, the test cells of the invention can be preserved by cryopreservation in a freezer (at −20° C. to −100° C.) or under liquid nitrogen (−176° C. to −196° C.).

SCREENING ASSAYS

The screening assays of the invention are designed to determine the effect of foods or food substances on the expression level of disease-related genes. Expression of a disease-related gene can be assessed directly by detecting and/or measuring the level of messenger RNA of the disease-related gene, or the level of the disease-related gene product. Where a reporter gene or fusion gene is operably associated with a disease-related gene regulatory region in a test cell, the transcriptional and/or translational activity of the region in the presence of foods or food substances can be determined by measuring the level of the reporter gene mRNA, the level of reporter molecule, or the signal generated by the reporter molecule.

Alternatively, expression of a disease-related gene can be determined indirectly by detecting and measuring the production or processing of other metabolite(s), where the production or processing reflects the expression and functional activity of the disease-related gene product. This approach is particularly applicable if the disease-related gene product is an enzyme, for example, a kinase which is capable of phosphorylating another protein. Such metabolites can be products of biochemical reactions that are downstream of a pathway in which the disease-related gene product is involved. Such alternative methods of detecting the expression of the disease-related gene or functional nucleotide sequence are intended to fall within the scope of the invention.

Expression of the disease-related gene in test cell can be detected or measured by nucleic acid-based detection techniques. Ribonucleic acid (RNA) from the test cell can be used as the starting point for such assay techniques, and can be isolated according to standard nucleic acid preparation procedures which are well known to those of skill in the art. RNA can be used in hybridization or amplification assays. If a sufficient quantity of the test cells can be obtained, standard Northern analysis can be performed to determine the level of messenger RNA expression of the disease-related gene.

Hybridization assays, such as Northern blot analysis, dot blot or slot blot hybridization, can involve for example, contacting and incubating RNA derived from test cells or tissue samples from transgenic animals with one or more labeled nucleic acid probes under conditions favorable for the specific annealing of these probes to their complementary sequences within the disease-related gene. Preferably, the lengths of these nucleic acid probes are at least 15 nucleotides. After incubation, all non-annealed nucleic acids are removed from the probe:disease-related transcript hybrid. The presence of nucleic acids which have hybridized, if any such molecules exist, is then detected. Appropriate nucleic acid probes to various disease-related genes can be obtained from public and commercial sources, or synthesized by well known chemical methods, or by amplification and subcloning into plasmid vectors, if the nucleotide sequence of the gene is available.

Using such a detection scheme, the nucleic acid from the cell type or tissue of interest can be immobilized, for example, to a solid support such as a membrane, or a plastic surface such as that on a microtiter plate or polystyrene beads. In this case, after incubation, nonannealed, labeled nucleic acid probes can be removed by washing the solid support. Detection or measurement of the remaining, annealed, labeled disease-related nucleic acid reagents is accomplished using standard techniques well-known to those in the art. Any appropriate isotopic and nonisotopic labels can be used. The amount of disease-related gene transcript to which the nucleic acid probes have annealed can be compared to the amount obtained from control cells which have not been exposed to the food or food substance.

Alternative detection methods for the detection of disease-related gene specific transcript, can involve their amplification, e.g., by polymerase chain reaction (PCR; Mullis, K. B., 1987, U.S. Pat. No. 4,683,202), followed by the detection of the amplified molecules using techniques well known to those of skill in the art. The resulting amplified sequences can be compared to those which would be obtained from test cells not exposed to the particular food or food substance. Quantitative PCR techniques can also be used to determine the absolute amount of disease-related gene transcript or the concentration of transcript relative to a standard (Wang et al., 1989, Proc Natl Acad Sci 86:9717–9721; Gilliland et al., 1990, Proc Natl Acad Sci 87:2725–2729). Multiplex PCR can be performed in which more than one disease-related gene transcript, or more than one portion of a disease-related gene transcript can be amplified from one sample simultaneously.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The preferred lengths of PCR primers are at least 9–30 nucleotides. For detection of the amplified product, the nucleic acid amplification can be performed using radioactively or non-radioactively labeled nucleotides. Alternatively, enough amplified product can be made such that the product can be visualized by standard ethidium bromide staining or by utilizing any other suitable nucleic acid staining method.

Techniques that involve amplification and hybridization are particularly useful when not all the disease-related gene transcripts are fully characterized. For example, when the assays are applied to screen for nutraceuticals that have an effect on the genes that are differentially expressed in abnormal cells, techniques such a& but not limited to differential display by PCR (Liang et al., 1992, Science 257:967–971; Pardee et al., U.S. Pat. No. 5,262,311), and serial analysis of gene transcript (SAGE; Velculescu et al., 1995, Science 270:484–487) may be used.

Those skilled in the art will be able to determine operative and optimal conditions for the above-described techniques by employing routine experimentation.

Once transgenic animals have been generated, the expression of the disease-related gene can be assayed utilizing standard techniques. The tissue or cell type to be analyzed will generally include those which are known, or suspected, to express the disease-related gene. Information relating to the temporal, tissue, cellular location of the disease-related gene activity can be obtained for example, using biopsy tissue. Initial screening can be accomplished by Southern blot analysis or PCR techniques to analyze animal tissues to assay whether integration of the transgene has taken place. The level of mRNA expression of the transgene in the tissues of the transgenic animals can be assessed using techniques which include but are not limited to Northern blot analysis of tissue samples obtained from the animal, in situ hybridization analysis, and reverse transcription-PCR (RT-PCR). It is possible to perform such disease-related gene expression assays "in situ", i.e., directly upon tissue sections (fixed and/or frozen) of tissue obtained from transgenic animal biopsies, such that no nucleic acid purification is necessary. See, for example, Nuovo, G. J., 1992, "PCR In Situ Hybridization: Protocols And Applications", Raven Press, N.Y.). Samples of tissue, can also be evaluated immunocytochemically using antibodies specific for the disease-related gene product or reporter molecule.

The present invention also provides protein-based screening assays which are based on the physical, immunological or functional properties of the gene product, reporter molecule, fusion protein or metabolite. The disease-related gene product, reporter molecule or metabolite can be isolated and purified by standard methods including chromatography and high pressure liquid chromatography based on, for example, ion exchange, affinity binding, size exclusion and hydrophobic interactions. Other standard techniques such as centrifugation, differential solubility and one- and two-dimensional gel electrophoresis can also be used. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Antibodies, or fragments of antibodies, such as those described below can be used to quantitatively or qualitatively detect by immunospecific binding the presence of disease-related gene product, reporter molecule, fusion protein or metabolite. This can be accomplished, for example, by immunofluorescence techniques employing a fluorescently labeled antibody coupled with light microscopic, flow cytometric, or fluorimetric detection. Flow cytometry and fluorescence activated cell sorting (FACS) are well-known method for assaying and separating cells based on their fluorescent properties (Kamarch, 1987, Methods Enzymol, 151:150–165). Separated cells can be directly deposited into individual wells of multi-well plates. These techniques are especially preferred if the disease-related gene products are expressed on the cell surface.

Immunoassays and non-immunoassays for disease-related gene products or reporter molecules will typically comprise incubating a sample; such as a biological fluid, a tissue extract, freshly harvested cells, test cell conditioned culture media or test cell lysates, in the presence of a detectably labeled antibody capable of identifying disease-related gene product or reporter molecule, and detecting the bound antibody by any of a number of techniques well-known in the art.

The biological sample can be brought in contact with and immobilized onto a solid phase support or carrier such as nitrocellulose, or other solid support which is capable of immobilizing cells, cell particles or soluble proteins. For Western blot analysis, the proteins has been separated by gel electrophoresis prior to immobilization to a membrane support. The support can then be washed with suitable buffers followed by treatment with the detectably labeled antibody. The solid phase support can then be washed with the buffer a second time to remove unbound antibody or fusion protein. The amount of bound label on solid support can then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The support material can have virtually any possible structural configuration so long as the coupled molecule is capable of binding to an antigen or antibody. Preferred supports include polystyrene beads. Those skilled in the art will know many other suitable carriers for binding antibody or antigen, or will be able to ascertain the same by use of routine experimentation.

For the production of antibodies specific for the disease-related gene product, reporter molecule, fusion protein, or metabolite, various host animals can be immunized by injection with the disease-related gene product, reporter molecule, metabolite or portions thereof. Such host animals can include but are not limited to rabbits, mice, and rats, to name but a few. Various adjuvants can be used to increase the immunological response, depending on the host species, including but not limited to Freund's (complete and incomplete), mineral gels, surface active substances, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed (Huse et al., 1989, Science, 246:1275–1281) to allow rapid and easy identification of monoclonal Fab fragments with the desired specificity. Any of the antibodies or fragments thereof so produced for the purpose of detecting expression of the disease-related gene product or reporter molecule may be included in a kit provided by the present invention.

One of the ways in which an antibody useful in the screening assays can be detectably labeled is by linking the antibody to an enzyme (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). In an enzyme immunoassay (EIA), the enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect the disease-related gene product through the use of a radioimmunoassay (RIA). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin or green fluorescent protein (GFP).

For example, antibodies directed to epitopes of the disease-related gene, reporter protein, metabolite can be used in vivo to detect the pattern and level of expression of the disease-related gene or reporter molecule in the body. Such antibodies can be labeled, e.g., with a radio-opaque or other appropriate compound and injected into a subject in order to visualize binding to the disease-related gene or reporter molecule expressed in the body using methods such as X-rays, CAT-scans, or MRI. In situ detection can be accomplished by removing a histological specimen from the transgenic animal and applying thereto a labeled antibody of the present invention. Using the present invention, those of ordinary skill will readily perceive that any of a wide variety of histological methods (such as staining procedures) can be modified in order to achieve such in situ detection.

Depending on the screening technique and nature of the signal used to assay the expression of a disease-related gene or reporter molecule, different reagents will be required. Any such reagents which may be used in any step of the screening assay may be included into a kit.

FOODS AND FOOD SUBSTANCES

Any matter that is normally ingested by humans or animals for sustenance, growth and maintenance of optimal health is considered as food that can be used as a source of nutraceuticals. Food contains both major and minor constituents. The major constituents are protein, fat, carbohydrates and fibers. Foods also contain minor constituents, such as minerals and vitamins. In addition, foods contain a large number of non-nutrient substances, i.e., compounds that have no known nutritional value.

In preferred aspects of the invention, non-nutritive substances are used in the screening assays. Such non-nutritive substances include a broad spectrum of compounds, such as secondary metabolites of plants and animals. Any compound produced by a plant, an animal, or a microorganism found in food, that is not necessary to perform the basic essential metabolic functions, such as energy conversion, respiration, and photosynthesis in the case of plants, can be considered a secondary metabolite. In plants, a range of compounds termed phytochemicals fall within this category, which include but are not limited to pigments, aromas, chemical defense molecules, such as phytoalexins; and the biosynthetic intermediates thereof. Phytochemicals found in edible plant and fungal materials, such as but not limited to fruits, vegetables, mushrooms, seaweeds, teas, spices, and herbs, constitute a rich source of nutraceuticals. Also encompassed in the invention are fermented foods, such as cheese, which contain compounds that are derived from microorganisms, such as yeast and bacteria. Many foods based on animals are also sources of nutraceuticals, which include but are not limited to invertebrates; such as jellyfish and shellfish; and vertebrates, such as fishes, reptiles, amphibians, birds, and mammals. For example, a range of oils derived from such animals can be used in the screening assay. Many of these compounds that are present in plant- or animal-derived foods or food substances may possess as yet unknown biological activities. Any such substance or compound in foods can be tested either in the foods in which they naturally occur, or in foods to which they have been added, or as isolated compounds. Some of the food substances are formed as a result of food processing, which, for example, can be achieved by pressure cooking, extrusion cooking, microwave cooking and other conventional methods. It is well known to those skilled in the art that these processing conditions generate new substances due to physical transformation of material and/or chemical reactions, like maillard reaction.

The methods of the invention for identifying nutraceuticals can be used with any foods or food substances. A mixture of uncharacterized food substances may be tested in the screening assays of the invention. Table 1 provides an exemplary list of representative food substances, including various classes of phytochemicals, that can be used in the screening assays, which is in no way intended to limit the food or food substances which can be used according to the present invention.

TABLE I

Examples of Food Substances

| Class | Compound | Source |
|---|---|---|
| Antioxidants | catechins | green tea |
| | theaflavins | black tea |
| | carnosol and carnosic acid | rosemary, sage |
| | tocopherol (Vit E) | oil seeds |
| | ascorbic acid (Vit C) | fruits, vegetables |
| Flavonoids | | |
| water soluble | flavonoids and their glycosides | onions, apple |
| organic soluble | methylated flavonoids | oranges |
| Phenolic acids | caffeic acid, its dimers and esters | coffee bean soy beans |
| | chlorogenic acid | coffee bean |
| | ferulic acid | fruits, soybean |
| | rosmaric acid | rosemary |
| Polyphenols | ellagic acid | strawberry |
| 1,2-Dicarbonyls | maltol and hydroxymaitol | malt |
| | 2,5-dimethyl-4-hydroxy-3(2H)furanone | pineapple |
| | 2-ethyl-5-methyl-4-hydroxy-3(2H)-furanone | soy sauce heated sugar |
| | cyclotene | |
| 1,3-Dicarbonyls | curcumin and demethoxycurcumin | tumeric |
| Isothiocyanates | sinigrin | mustard |
| | allyl isothiocyanate | cabbage |

TABLE I-continued

Examples of Food Substances

| Class | Compound | Source |
|---|---|---|
| glucosinolates | phenethyl isothiocyanate | watercress |
| | benzyl isothiocyanate | garden cress |
| | sulforaphane | broccoli |
| Terpenes | | |
| monoterpenes | limonene | orange |
| | carvone | caraway seeds |
| triterpenes | glycyrrhizin, glycyrrhizinic acid | licorice *Boswellia serrata* |
| Pseudoestrogens | genistein | soybean |
| | daidzin | soybean |
| Sulfur compounds | allyl sulfides | garlic |
| | alliin | garlic |
| | deoxyallin | garlic |
| | ajoene | garlic oil |
| | propenyl sulfides | onions |
| Carotenoids | beta-carotene | carrot |
| | lycopene | tomato |
| | capsanthin | paprika |
| | astacin | lobster shell |
| Others | polyacetylenes | vegetables |
| | coumarins | vegetables |
| | peptides | cheese |
| | catechol analogs | ginger |
| | flavor compounds | |
| | conjugated linoleic acid (CLA) | cheese |

Many of these food substances are structurally related, and are grouped into families, such as but are not limited to allylic sulfur-containing compounds, terpenes, glucosinolates, flavonoids, and carotenoids. For example, terpenes are widely distributed in a variety of fruit oils, such as orange, grapefruit, lemon, lime and bergamot oils. D-limonene is one of the most widely distributed of the monocyclic terpenes and occurs in citrus, mint, myristica, caraway, thyme, cardamon, and coriander.

The techniques for fractionation and isolation of food substances and active compounds, such as phytochemicals, are well known to those skilled in the art and are described in standard treatises. See, for example, Food Phytochemicals for Cancer Prevention, Vol. I and II, Published by the American Chemical Society, Washington, D.C. 1994 (Vol I, editors Huang, Osawa, Ho and Rosen, Chapters 7, 14, 20 and 27; Vol II, editors Ho, Osawa, Huang and Rosen, Chapters 23 and 24. Any of these techniques may be used in combination with the screening assays of the present invention for systematically identifying and isolating the compounds in foods that are capable of modulating disease-related gene expression.

Depending on the chemical properties of the phytochemicals, a suitable solvent or solvents can be used to extract the phytochemicals from the respective sources. The extract will then be successively chromatographed using various adsorbents. Generally, chromatography is used for the separation of phytochemicals, and spectrometric or spectroscopic techniques used for the identification of the phytochemicals. Infrared (IR), mass spectrometry (MS) and nuclear magnetic resonance (NMR) techniques are preferred techniques for identification. NMR is generally more useful when analyzing an unknown species that is reasonably pure after isolation. MS is used for the identification of minor or trace components in mixtures, such as foods, since it can be coupled with chromatographic or separation techniques, such as gas chromatography (GC) and high performance liquid chromatography (HPLC).

ADMINISTRATION OF NUTRACEUTICALS

The data obtained from the cell culture assays and animal model studies can be used in formulating a range of dosage for use in humans or animal subjects. More than one nutraceuticals can be used in combination to achieve a particular healthful benefit. The dosage of such nutraceuticals lies preferably within a range of circulating concentrations that include the $ED_{50}$ (i.e., the concentration of the test compound to which 50° of the population responds) with little or no toxicity. The dosage may vary within this range depending upon the dosage form employed and the route of administration utilized. For any compound used in the method of the invention, the effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans or animal subjects. Levels in plasma can be measured, for example, by high performance liquid chromatography.

Nutraceutical compositions for use in accordance with the present invention can be formulated in a manner similar to food supplement using one or more fillers, or conventional pharmaceuticals using one or more physiologically acceptable carriers or excipients.

Thus, the nutraceuticals can be formulated for administration by inhalation or insufflation (either through the mouth or the nose) or oral, buccal, parenteral or rectal administration. For oral administration, the nutraceuticals can be added directly to foods so that the nutraceuticals are ingested during normal meals. Any methods known to those skilled in the art may be used to add or incorporate nutraceuticals to natural or processed foods.

The nutraceutical compositions can also take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also be made to resemble foods, containing buffer salts, flavoring, coloring and sweetening agents as appropriate.

Preparations for oral administration can be suitably formulated to give controlled release of the active nutraceutical compound.

For buccal administration the nutraceutical compounds can take the form of tablets or lozenges formulated in conventional manner.

For administration by inhalation, the nutraceutical for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The nutraceuticals can be formulated for parenteral administration by injection, e.g., by bolus injection or continuous infusion. Formulations for injection can be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The nutraceuticals can also be formulated in rectal compositions such as suppositories or retention enemas, e.g., containing conventional suppository bases such as cocoa butter or other glycerides.

In addition to the formulations described previously, the nutraceuticals may also be formulated as a depot preparation. Such long acting formulations may be administered by implantation (for example subcutaneously or intramuscularly) or by intramuscular injection. Thus, for example, the nutraceutical may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active nutraceutical. The pack can for example comprise metal or plastic foil, such as a blister pack. The pack or dispenser device may be accompanied by instructions for administration.

NUTRACEUTICALS IN FOODS

The present invention further provides for processed foods or foods substances in which nutraceuticals have been added, generated, or fortified. More than one nutraceutical may be included in the processed food or food substance, such that additive and synergistic effects of the combination of nutraceuticals, which are more favorable and different from the individual nutraceutical, can be obtained. Methods for adjusting the level of nutraceuticals in foods during food processing are also encompassed by the invention.

Typically, food processing consists of three main stages: 1) preliminary operations, 2) conversion operations and 3) preservation operations. See generally, Brennan et al., in Food Engineering operations, 3rd edition, Elsevier Applied Science, London and New York, 1990, pages 3–683; The technology of Extrusion Cooking, edited by N. D. Frame, 1994, pages 1–251; Principles of Food Science, edited by Owen R. Fennema, Marcel Dekker Inc., 1975, pages 1–467, which are incorporated herein by reference in their entirety. Preliminary operations consists of a) selection of raw materials based on their physical and functional properties; b) cleaning of raw material, and c) sorting and grading. Conversion operations can consist of a) size reduction and screening of solids, b) mixing and emulsification, c) filtration and membrane separation, d) centrifugation e) solid liquid extraction and expression and e) crystallization. Preservation operations can consist of a) heat processing b) evaporation, c) dehydration, d) freezing, e) irradiation, and f) storage.

In one embodiment of the invention, processed foods containing an increased level of a nutraceutical for comsumption by a subject can be prepared by (1) contacting a food or food substance with test cells containing a disease-related gene or portion thereof for an interval sufficient for a nutraceutical to modulate the expression of the disease-related gene or portion thereof; (2) measuring the expression of the disease-related gene; (3) comparing the level of expression with that of a control cell which was not contacted with the nutraceutical; and (4) adding an appropriate amount of the nutraceutical in the processed food. Nutraceuticals can be added to raw or processed food materials in the form of food additives. For example, one or more nutraceuticals encapsulated in liposomes can be added to food during processing.

Some nutraceuticals are naturally present in foods or food substances, in which case, such compounds are fortified by changing the composition of the foods or food substances to preserve the compounds, or by eliminating or reducing exposure to processes that will reduce the level of nutraceutical compounds in the foods. For example, boiling vegetables can change the composition of phytochemicals while freeze-drying may preserve the original composition in the vegetables. In some instances, nutraceuticals can be generated during processing in the foods or food substances by including additional ingredients and/or by adjusting the conditions of the relevant process steps. For example, processes commonly used for enhancing or regenerating flavors and aromas of fresh foods can be applied, since some nutraceuticals are structurally related to compounds that impart flavors and aromas of foods. Other processes for generating nutraceuticals can include treatment of foods by microbial enzymes such as but not limited to lipases, esterases, amylases, proteases, and phosphatases.

Plant-derived nutraceuticals can be prepared by plant cell culture or intact plants. Pressing, distillation, extraction and chromatography can be used to isolate nutraceuticals from intact plant parts. Plant cell suspension cultures can also be used for the synthesis of nutraceuticals, in which the compounds can be produced, harvested, and isolated by established fermentation technologies.

The present invention also encompasses foods or food substances that contain a level of nutraceutical or a precursor thereof higher than naturally occurring form of the foods or food substances. A precursor of a nutraceutical is a compound that can be converted into the nutraceutical during food processing. Such foods or food substances can be derived from organisms that have been treated to induce the production of the nutraceutical. The nutraceutical-producing plant or animal can be selected by conventional breeding methods. The nutraceutical-producing plant or animal can also be modified by recombinant DNA technologies.

Exposure of plants to different environmental conditions, such as light, drought, salinity, soil composition, temperature, chemical stress, and presence of pathogen; can induce or increase the production of nutraceuticals, which are secondary metabolites. The necessary conditions required to induce or increase the production of nutraceuticals in plants can be determined by one skilled in the art with routine experimentation.

Conventional plant breeding methods change their genetic properties by combining the desirable genetic traits of different but related species or varieties of plants either by sexual mating or by somatic cell fusion. Gene mutations can also be induced in plants by treatment with chemicals and radiation, or by culturing plant cells and selecting for somaclonal variants. Such breeding methods are well known to those skilled in the arts, and can be applied to selecting plants that produce a higher yield of the nutraceuticals.

Since a significant number of nutraceuticals are phytochemical compounds which are products of plant secondary metabolism, recombinant DNA techniques can be applied to modify one or more of those plant genes that encode components of the secondary metabolic pathway. The components of such a biochemical pathway are mostly biosynthetic enzymes, of which their turnover rates, maximal activities, and substrate specificities can be modified, for example, by mutagenesis of the protein-coding regions. Alternatively, the level of expression of such genes can be modified by manipulating the regulatory regions that control their expression, or by expression of an antisense messenger RNA that interferes with the translation of the normally functional gene transcript (Kramer et al., 1989, Trends in Biotech 7:190–194). Any transgenic plants that are so modified such as to increase the level of nutraceuticals or the precursors thereof are encompassed by the present invention.

Transgenic plant cell cultures or intact plants can be generated by any techniques well known to those skilled in the arts. For general reviews of plant molecular biology techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

Viral promoters such as the 35S RNA and 19S RNA promoters of CaMV (Brisson et al. 1984, Nature 310:511–514), or the coat protein promoter of TMV (Takamatsu et al. 1987, EMBO J. 6:307–311) may be used to express the plant transgene; alternatively, plant promoters such as the small subunit of RuBISCo (Coruzzi et al. 1984, EMBO J. 3:1671–1680; Broglie et al. 1984, Science 224:838–843); or heat shock promoters, e.g., soybean hsp17.5-E or hsp17.3-B (Gurley et al. 1986, Mol. Cell. Biol. 6:559–565) may be used.

Plant that can be genetically manipulated to modulate the level of nutraceuticals may include, but are not limited to, those of maize, wheat, rice, soybean, tomato, tobacco, carrots, peanut, potato, sugar beets, sunflower, yam, Arabidopsis, and rape seed. Both plant cells and protoplasts may be used for transformation. Plant protoplasts are preferred because of the absence of a cell wall, and their potential to proliferate as cell cultures, and to regenerate into a plant.

In addition, the recombinant constructs containing the plant transgene may comprise plant-expressible selectable or screenable marker genes which include, but are not limited to, genes that confer antibiotic resistances, (e.g., resistance to kanamycin or hygromycin) or herbicide resistance (e.g., resistance to sulfonylurea, phosphinothricin, or glyphosate). Screenable markers include, but are not limited to, genes encoding β-glucuronidase (Jefferson, 1987, Plant Molec Biol. Rep 5:387–405), luciferase (Ow et al. 1986, Science 234:856–859), and B protein that regulates anthocyanin pigment production (Goff et al. 1990, EMBO J 9:2517–2522).

To introduce recombinant DNA constructs into plant cells, the Agrobacterium tumefaciens system for transforming plants may be used. The proper design and construction of such T-DNA based transformation vectors are well known to those skilled in the art. Such transformations preferably use binary Agrobacterium T-DNA vectors (Bevan, 1984, Nuc. Acid Res. 12:8711–8721), and the co-cultivation procedure (Horsch et al. 1985, Science 227:1229–1231). Generally, the Agrobacterium transformation system is used to engineer dicotyledonous plants (Bevan et al. 1982, Ann. Rev. Genet 16:357–384; Rogers et al. 1986, Methods Enzymol. 118:627–641), but it may also be used to transform as well as transfer DNA to monocotyledonous plants and plant cells. (see Hernalsteen et al. 1984, EMBO J 3:3039–3041; Hooykass-Van Slogteren et al. 1984, Nature 311:763–764; Grimsley et al. 1987, Nature 325:1677–1679; Boulton et al. 1989, Plant Mol. Biol. 12:31–40.; Gould et al. 1991, Plant Physiol. 95:426–434).

In other embodiments, various alternative methods for introducing recombinant nucleic acid constructs into plant cells may also be utilized. These other methods are particularly useful where the target is a monocotyledonous plant cell. Alternative gene transfer and transformation methods include, but are not limited to, protoplast transformation through calcium-, polyethylene glycol (PEG)—or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; Gordon-Kamm et al., 1990, Plant Cell 2:603–618).

EXAMPLE: IDENTIFICATION OF NUTRACEUTICALS THAT REGULATE DISEASE-RELATED GENE EXPRESSION

This example evaluates the ability of a variety of food substances isolated from various foods to modulate the expression of a disease-related gene, lysyl oxidase (LOX).

Lysyl oxidase (LOX) is a copper-dependent amine oxidase that catalyzes the formation of lysine-derived crosslinks in collagen and elastin. The level of lysyl oxidase activity has a profound effect on tissue function, cell differentiation and cell growth. Reduced levels of lysyl oxidase are known to result in increased tumor production and in the development of blood vessel defects. Thus, up-regulation of the lysyl oxidase gene would serve to counter these disorders.

It has been shown that expression of the human lysyl oxidase (LOX) gene is regulated by sequences located 5' to the gene as well as in the first intron (Csiszar et al., Molec Biol Reports, in press). Using a reporter construct containing the promoter domain and first intron of the human LOX gene joined to the chloramphenicol acetyltransferase (CAT) reporter gene, the effect of several food substances including antioxidants, flavor and color compounds on the transcriptional activity of the human lysyl oxidase gene was assayed in cultured human cells (LOXCAT cells).

The results below clearly demonstrate the feasibility and usefulness of the methods provided by the present invention for assaying nutraceuticals for a direct effect on the expression of a human gene associated with colon cancer. Of the first seven food substances screened in this preliminary study, two resulted in a dramatic up-regulation of LOX gene expression.

MATERIALS AND METHODS

Human osteosarcoma cells (Samid et al., 1989, Clinical Biotech 1:21–26) were transfected with a CAT construct that is based on the vector psk-CAT (Promega, Madison, Wis.) and contained the human lysyl oxidase gene promoter and the complete first intron. The intron is known to contain consensus sequences for numerous transcription factor binding sites and regulatory elements, and proved to have an enhancer activity. CAT constructs were transfected into confluent preparations of cultured cells using the calcium phosphate precipitation technique (Ausubel et al., supra). Transfected cells referred to as LOXCAT cells, were exposed for 20 hours to various food substances at different concentrations and harvested. Cell lysates were used to measure chloramphenicol acetyltransferase activity as the conversion of $^{14}$C-chloramphenicol to its acetylated forms which are quantitated by thin layer chromatography and scintillation counting.

The following non-nutritive food substances were selected for testing: epigallocatechin gallate (a polyphenol found in tea), and carnosol (from rosemary and sage), both of which are recognized as antioxidants; kojic acid (brown gravy), maltol (ginseng, brown gravy), and tangeretin (citrus), representing flavor substances; wheat protein hydrolysate; and curcumin (from tumeric), a known color substance. Epigallocatechin gallate, kojic acid, maltol, tangeretin, curcumin and wheat protein hydrolysate were purified by standard techniques as described in Section 5.4.

The results presented are a ratio of CAT activity in transfected cell in the presence of food substances relative to the basic CAT activity in the absence of added food substance. The basic CAT activity is expressed as a value of 1.0 (represented as L0). SV40 is a control CAT recombinant that contains the SV40 promoter. Assays were performed in the presence of different concentrations of nutraceuticals.

RESULTS

The results of the LOX-CAT assay are summarized in FIG. 1. Tangeretin and epigallocatechin gallate are the most potent activators of LOX gene expression in the group; both compounds mediated a dose dependent, five fold stimulation of CAT activity. Increasing tangeretin concentration had an inverse effect in that 10 µg induced a 5-fold increase in activity, while at 20 µg/ml, the increase was 2.7 fold. Epigallocatechin gallate also showed a concentration dependent effect producing a 4.45 and 4.7 fold increase in promoter activity at 100 and 200 µg/ml respectively. Some of the compounds, such as kojic acid were toxic when added to the cultured cells even though the presence of 10 µg/ml kojic acid raised the promoter activity by 2.3 fold. Other food substances such as a wheat extract actually resulted in decreased CAT activity even though cell growth was enhanced. Curcumin and maltol both increased the activity of the promoter in a concentration-dependent manner. These results clearly demonstrate the feasibility of assaying nutraceuticals for a direct effect on human gene expression.

Since reduced levels of LOX will result in an increase in tumors and in causing blood vessel defects, the above food substances showed the potential to counteract the development of these disorders through up-regulation of LOX gene expression. Including food substances such as tangeretin and epigallocatechin gallate into the diet could modulate LOX gene expression in the colonic epithelium, thereby counteracting the development of hyperproliferative cells that form as a result of somatic mutations in the LOX gene.

Using the method and test cells provided herein, one will be able to screen a significant number of other food or food substances for their effect(s) in modulating the expression of LOX and other genes relevant to, for example, colon cancer, such as p53, DCC, APC and MCC. Changes in expression levels of such genes mediated by selected food substances will be tested for actual phenotypic changes in an animal model of colon cancer.

It is also envisioned that this screening procedure can be expanded to include various candidate genes known to be involved in the development of other diseases and adapted to identify the altered expression of unknown genes relevant to the pathogenesis of established human diseases.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

A number of references are cited herein, the entire disclosure of which are incorporated herein, in their entirety by reference.

We claim:

1. A method for identifying a non-nutrient food substance that is capable of modulating the expression of a disease-related gene comprising:
   (a) contacting a non-nutrient food substance with a test cell containing a disease-related gene or portion thereof for an interval sufficient for the non-nutrient food substance to modulate expression of the disease-related gene or portions thereof; and
   (b) measuring the expression of the disease-related gene or portions thereof, in which an increase or decrease in the expression, as compared to that of a control cell containing the disease-related gene or portion thereof which was not contacted with the non-nutrient food substance, indicates that the non-nutrient food substance modulates the expression of the disease-related gene.

2. A method for isolating a non-nutrient food substance from a food comprising a mixture of nutrient and non-nutrient food substances, said non-nutrient food substance being capable of modulating the expression of a disease-related gene comprising:
   (a) fractionating a food comprising a mixture of nutrient and non-nutrient food substances into nutrient-containing and non-nutrient containing fractions;
   (b) contacting a non-nutrient food substance containing fraction of the food with a test cell containing a disease-related gene or portions thereof for an interval sufficient for a non-nutrient food substance in the fraction to modulate expression of the disease-related gene or portions thereof;
   (c) measuring the expression of the disease-related gene or portions thereof, in which an increase or decrease in the expression, as compared to that of a control cell containing the disease-related gene or portion thereof which was not contacted with the fraction, indicates that the non-nutrient food substance in the fraction modulates the expression of the disease-related gene; and
   (d) isolating the non-nutrient food substance from the fraction identified in step (c).

3. A method for identifying a food or food substance that is capable of increasing expression of a disease-related gene comprising:
   (a) contacting a food or food substance comprising a mixture of nutrient and non-nutrient food substances with a pathologic test cell in which underexpression of a disease-related gene is associated with pathology of the cell, for an interval sufficient for the food to increase the expression of the disease-related gene; and
   (b) measuring the expression of the disease-related gene, wherein an increase in the expression, as compared to that of a pathologic control cell in which the disease-related gene is underexpressed and which was not contacted with the food, indicates that the food or food substance increases the expression of the disease-related gene.

4. A method for identifying a food or food substance, that is capable of decreasing the expression of a disease-related gene comprising:
   (a) contacting a food or food substance comprising a mixture of nutrient and non-nutrient food substances with a pathologic test cell in which overexpression of a disease-related gene is associated with the pathology of the cell, for an interval sufficient for the food to decrease the expression of the disease-related gene; and
   (b) measuring the expression of the disease-related gene, wherein a decrease in the expression as compared to that of a pathologic control cell in which the disease-related gene is overexpressed and which was not contacted with the food, indicates that the food or food substance decreases the expression of the disease-related gene.

5. The method of claim 1, 2, 3, or 4, wherein the non-nutrient food substance is a secondary metabolite of a plant.

6. The method of claim 1, 2, 3, or 4, wherein the non-nutrient food substance is a result of food processing.

7. The method of claim 1, 2, 3, or 4, wherein the non-nutrient food substance is a result of food fermentation.

8. The method of claim 1, 2, 3, or 4, wherein the test cell is a cancer cell and the disease-related gene is associated with a multi-step genetic process leading to cancer.

9. The method of claim 8, wherein the disease-related gene is a protooncogene or a tumor suppressor gene.

10. The method of claim 9, wherein the disease-related gene is a tumor suppressor gene selected from the group consisting of lysyl oxidase, ras, BRCA1, BRCA2, APC, MCC, DCC, Rb, and p53.

11. The method of claim 1, 2, 3, or 4, wherein the disease-related gene is associated with a disease selected from the group consisting of cardiovascular disease, respiratory disease, disease of the kidney, disease of the pancreas, disease of the liver, gastrointestinal disease, hematological disease, metabolic disease, neurological disease, aging, immune disease, disease of the reproductive system, and infectious disease.

12. The method of claim 1, 2, 3, or 4, wherein the disease-related gene is associated with fatigue, obesity, infertility, pregnancy, menopause, allergy, acute inflammation, chronic inflammation, transplant rejection, wound healing, sleep disorder, substance dependence, or behavioral disorder.

13. The method of claim 1, 2, 3, or 4, wherein the disease-related gene is a human gene.

14. The method of claim 1, 2, 3, or 4, wherein the non-nutrient food substance comprises a terpene, carotenoid, flavonoid, polyphenol, allylic sulfur-containing compound, antioxidant, pseudoestrogen, or glucoinolate.

15. The method of claim 1, 2, 3, or 4, wherein the test cell is derived from an individual human.

16. The method of claim 1, 2, 3, or 4, wherein the test cell is derived from a cell line.

17. The method of claim 1, 2, 3, or 4, wherein the test cell is derived from an animal model of a human disease or undesirable condition.

18. The method of claim 1, 2, 3, or 4, wherein the test cell is derived from a transgenic animal, in which the disease-related gene is a transgene.

19. A method for identifying a non-nutrient food substance that is capable of modulating the expression of the LOX gene comprising:

(a) contacting a non-nutrient food substance with a LOX-CAT cell containing the LOX gene or a portion thereof for an interval sufficient for the non-nutrient food substance to modulate expression of the LOX gene or a portion thereof; and (b) measuring the expression of the LOX gene or portion thereof, in which an increase or decrease in the expression, as compared to that of a control LOXCAT cell containing the LOX gene or portion thereof which was not contacted with the non-nutrient food substance, indicates that the non-nutrient food substance modulates the expression of the LOX gene.

20. The method of claim 1, 2, 3, or 4, wherein the expression of the disease-related gene is measured by the level of messenger RNA of the disease-related gene.

21. The method of claim 1, 2, 3, or 4, wherein the expression of the disease-related gene is measured by the level of disease-related gene product.

22. The method of claim 1, 2, 3, or 4, wherein the expression of the disease-related gene is measured by the functional activity of the disease-related gene.

23. The method of claim 1, 2, 3, or 4, wherein the expression of the disease-related gene is measured by the level of a metabolite that is dependent on the functional activity of the disease-related gene product.

24. The method of claim 1, 2, 3, or 4, wherein the expression of the disease-related gene is measured by immunospecific binding of the disease-related gene product to an antibody specific for the disease-related gene product.

25. The method of claim 1 or 2, wherein the test cell contains a reporter gene operably associated with the regulatory regions of the disease-related gene.

26. The method of claim 1 or 2, wherein the test cell contains a reporter gene which comprises the disease-related gene which is modified to encode a reporter moiety.

27. The method of claim 25, wherein the expression of the disease-related gene is measured by the level of messenger RNA of the reporter gene.

28. The method of claim 26, wherein the expression of the disease-related gene is measured by the level of messenger RNA of the reporter gene.

29. The method of claim 25, wherein the expression of the disease-related gene is measured by the level of the product of the reporter gene.

30. The method of claim 26, wherein the expression of the disease-related gene is measured by the level of the product of the reporter gene.

31. The method of claim 25, wherein the expression of the disease-related gene is measured by the functional activity of the product of the reporter gene.

32. The method of claim 26, wherein the expression of the disease-related gene is measured by the functional activity of the product of the reporter gene.

33. The method of claim 25, wherein the expression of the disease-related gene is measured by immunospecific binding of a reporter molecule to an antibody specific for the product of the reporter gene.

34. The method of claim 26, wherein the expression of the disease-related gene is measured by immunospecific binding of a reporter molecule to an antibody specific for the product of the reporter gene.

35. The method of claim 25, wherein the test cell is derived from a transgenic animal, in which the reporter gene is a transgene.

36. The method of claim 26, wherein the test cell is derived from a transgenic animal, in which the reporter gene is a transgene.

37. The method of claim 1, 2, 3, or 4, wherein the expression of the disease-related gene is measured by Northern blot analysis, dot blot hybridization, or quantitative polymerase chain reaction.

38. The method of claim 25, wherein the expression of the disease-related gene is measured by chloramphenicol acetyltransferase assay, β-galactosidase assay, alkaline phosphatase assay, glucuronidase assay, or by light emitted by the product of the reporter gene.

39. The method of claim 26, wherein the expression of the disease-related gene is measured by chloramphenicol acetyltransferase assay, β-galactosidase assay, alkaline phosphatase assay, glucuronidase assay, or by light emitted by the product of the reporter gene.

40. The method of claim 1, 2, 3, or 4, wherein the disease-related gene encodes an oncogenic protein, a signal transducing protein, an acute phase protein, a transcription factor, a DNA repair protein, a cell cycle protein, a complement protein, a cell adhesion protein, a cytokine, a cytokine receptor, a neurotransmitter receptor, an extracellular matrix protein, a matrix metalloprotease, an endothelial cell protein, a lipoprotein or enzyme involved in lipid metabolism, a coagulation factor, or a fibrinolytic factor.

41. The method of claim 1, 2, 3, or 4, wherein the disease-related gene is associated with insulin-dependent diabetes, multiple sclerosis, rheumatoid arthritis, or systemic lupus erythematous.

42. The method of claim 9, wherein the disease-related gene is a protooncogene selected from the group consisting of fos, jun, sis, and erb.

43. A method for isolating a non-nutrient food substance from a food comprising a mixture of nutrient and non-nutrient food substances, said non-nutrient food substance being capable of modulating the expression of the LOX gene comprising:

(a) fractionating a food comprising a mixture of nutrient and non-nutrient food substances into nutrient-containing and non-nutrient containing fractions;

(b) contacting a non-nutrient food substance containing fraction of the food with a LOXCAT cell containing the LOX or portions thereof for an interval sufficient for a non-nutrient food substance in the fraction to modulate expression of the LOX gene or portions thereof;

(c) measuring the expression of the LOX gene or portions thereof, in which an increase or decrease in the expression, as compared to that of a control LOXCAT cell containing the LOX gene or portion thereof which was not contacted with the fraction, indicates that the non-nutrient food substance in the fraction modulates the expression of the LOX gene; and (d) isolating the non-nutrient food substance from the fraction identified in step (c).

* * * * *